United States Patent [19]

Hudyma et al.

[11] Patent Number: 5,106,842

[45] Date of Patent: Apr. 21, 1992

[54] ANTIBIOTIC C-3 CYCLOBUTENEDIONE SUBSTITUTED (1-CARBA)CEPHALOSPORIN COMPOUNDS, COMPOSITIONS, AND METHODS OF USE THEREOF

[75] Inventors: Thomas W. Hudyma, Durham; Richard A. Partyka, Killingworth, both of Conn.

[73] Assignee: Bristol-Myers Squibb Co., New York, N.Y.

[21] Appl. No.: 600,656

[22] Filed: Oct. 22, 1990

[51] Int. Cl.$^5$ ............... C07D 501/24; A61K 31/545
[52] U.S. Cl. .................... 514/202; 540/222; 540/221; 540/229; 540/215; 514/201
[58] Field of Search ............... 540/222, 221; 514/202, 514/201

[56] References Cited

U.S. PATENT DOCUMENTS

| | | | |
|---|---|---|---|
| 4,496,560 | 1/1985 | Farge et al. | 514/204 |
| 4,508,717 | 4/1985 | Berger et al. | 514/203 |

FOREIGN PATENT DOCUMENTS

| | | |
|---|---|---|
| 0154253 | 9/1985 | European Pat. Off. |
| 0211540 | 2/1987 | European Pat. Off. |
| 0327239 | 8/1990 | European Pat. Off. |

OTHER PUBLICATIONS

Crowell, et al., *Journal of Medicinal Chemistry*, 32, p. 2436 (1989) "3-Sulfonyl-1-carba-1-dethiacephems".
Fahey, et al., *Journal of Medicinal Chemistry*, 19, 4, p. 562 (1976) "3-Cyanocephems, and Carbon-13 Heterocyclic-Substituted Cephems via 1,3-Dipolar Cycloadditions".
Sugawara, et al., *Chem. Parm. Bull.*, 28, 7, p. 2116 (1980) "Synthesis of Cephalosporins with Substituted Thiadiazoles Directly Attached to the C-Position".
Hornback, et al., Copy of abstract No. 153 and hand out from the 200th American Chemical Society Meeting in Washington, D.C., Aug. 26–31, 1990.
Farina, et al., *The Journal of Organic Chemistry*, 54, 20, p. 4962 (1989) "A General Route to 3-Functionalized 3-Norcephalosporins".
Hatanaka, et al., *Tetrahedron Letters*, 24, 44, p. 4837 (1983) "A Simple Synthesis of (±)-1-Carbacephem Derivatives".
Farina, et al., *Tetrahedron Letters*, 29, 47, p. 6043 (1988) "Palladium Catalysis in Cephalosporin Chemistry: A Versatile New Approach to 3-Substituted Cephems".
Cook, et al., *The Journal of Organic Chemistry*, 54, p. 5828 (1989) "Palladium-Catalyzed Chemistry of B-Lactam Vinyl Triflates".

*Primary Examiner*—Nicholas S. Rizzo
*Attorney, Agent, or Firm*—William T. Han

[57] ABSTRACT

A compound of formula I

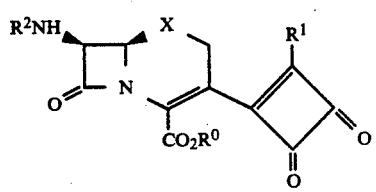

wherein
X is sulfur or $CH_2$;
$R^1$ is hydrogen, hydroxy, amino, $C_{1-6}$ alkyl, $C_{2-6}$ alkenyl, $C_{2-6}$ alkynyl, phenyl optionally substituted with one to three $C_{1-6}$ alkyl, $C_{1-6}$ alkyloxy or hydroxy, $C_{1-6}$ alkylthio, phenylthio optionally substituted with one to three $C_{1-6}$ alkyl or $C_{1-6}$ alkyloxy on the phenyl ring, phenylmethyloxy optionally substituted with one to three $C_{1-6}$ alkyl or $C_{1-6}$ alkyloxy on the phenyl ring, 1-morpholino, $C_{1-6}$ alkyloxy, $C_{2-6}$ alkenylmethyloxy, $C_{3-6}$ alkynylmethyloxy, $C_{1-6}$ alkylamino, $C_{1-6}$ dialkylamino or a radical selected from the group consisting of

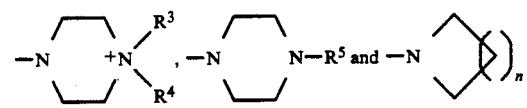

in which n is 0 to 3, $R^5$ is $C_{1-6}$ alkyl or hydrogen, and $R^3$ and $R^4$ are independently $C_{1-6}$ alkyl;
$R^2$ is hydrogen, a conventional amino protecting group or an acyl group;
$R^0$ is hydrogen or a conventional carboxy protecting group, or $-CO_2R^0$ taken together forms a physiologically hydrolyzable ester; or
pharmaceutically acceptable salts or solvates thereof.

13 Claims, No Drawings

ANTIBIOTIC C-3 CYCLOBUTENEDIONE SUBSTITUTED (1-CARBA)CEPHALOSPORIN COMPOUNDS, COMPOSITIONS, AND METHODS OF USE THEREOF

BACKGROUND OF THE INVENTION

1. Field of Invention

This invention relates to novel 1-carba(1-dethia)-3-cephem-4-carboxylic and 3-cephem-carboxylic acid derivatives which contain unique 3,4-dioxo-1-cyclobutenyl moieties in the C-3 position. The compounds of the instant invention were found to possess potent antibacterial activity. Thus, in another aspect, this invention relates to their antibiotic use and pharmaceutical compositions. Also included within the scope of the present invention are useful intermediates for the synthesis of said antibiotics.

2. Nomenclature and Numbering

Formula I below represents compounds of the present invention; the numbering therein shows the convention used in this application

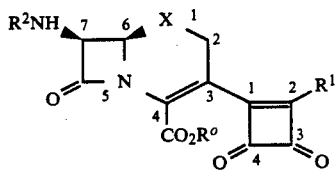

and follows the most widely system used in the art. In formula I, a class of compounds having X as sulfur will be referred to as 3-cephem-carboxylic acids, or simply as cephalosporins. On the other hand when X is $CH_2$, the class will be named as 1-carba(1-dethia)-3-cephem-4-carboxylic acids, or simply as 1-carbacephalosporins. defined hereinbelow.

3. Description of Related Art

In the antibiotic arts, there has long been a need for new and effective antibiotic compounds. Due to rapid changes in pathogens, for which treatment with the antibiotic compounds are required, the older and more used antibiotics often become either ineffective or significantly less effective against the pathogens. Effective antibiotics are therefore in constant demand to replace the older and more used antibiotics.

Because of the above mentioned long felt need in this art for more potent and effective antibiotics, many cephalosporin compounds and their derivatives, including 1-carbacephalosporins have been synthesized and tested for appropriate antibiotic properties. One hypothesis leading toward more potent antibacterial agents is to attach electron withdrawing groups on the C-3 positions with hopes of increasing the acylating potential of the β-lactams, such as the prototypes cefaclor and loracarbef having the following structure.

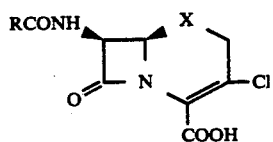

cefaclor: R = phenylglycyl, X = S
loracarbef: R = phenylglycyl, X = $CH_2$

Examples of other compounds, which have C-3 electron withdrawing substituents appear in the following patents and printed publications:

(a) European Application 154,253 published on Feb. 20, 1984 discloses carbacephalosporins of the formula

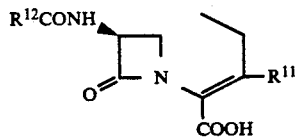

wherein $R^{11}$ is a lower alkylsulfonyloxy, unsubstituted or substituted arylsulfonyloxy, azido, cyano, carbamoyloxy, unsubstituted or substituted heterocyclic thio, unsubstituted or substituted lower alkylthio, or unsubstituted or substituted arylthio group; $R^{12}$ is a group represented by the formula

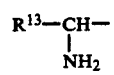

in which $R^{13}$ is an unsubstituted or substituted phenyl, or 2-aminothiazolyl group, or a group represented by the formula

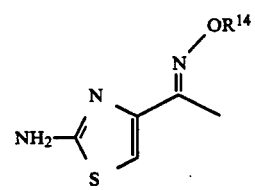

in which $R^{14}$ is an unsubstituted or substituted lower alkyl group.

(b) Cromwell et al., in the *Journal of Medicinal Chemistry*, 32, p. 2436 (1989) discloses, inter alia, other 3-sulfonyl-1-carbacephalosporins represented by the general formula

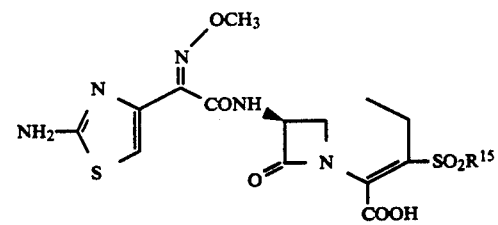

wherein $R^{15}$ is cyclopropyl, 2-thienyl, 3-pyridyl, and 4-(3,5-Me$_2$)isoxazolyl.

(c) European Application 327,239 published on Jan. 25, 1988, discloses, inter alia, 1-carbacephalosporins of the formula

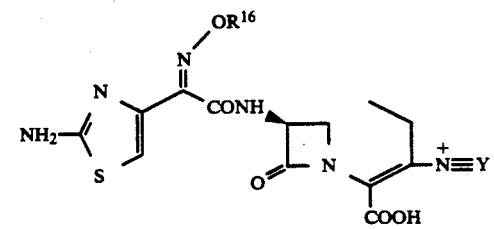

wherein the radical

is a quaternary ammonium group that may be acyclic, cyclic, or a combination of the two, and may contain one or more additional hetero atoms selected from nitrogen, sulfur and oxygen; $R^{16}$ is hydrogen, $C_{1-4}$ alkyl, or a carboxy-substituted alkyl or cyloalkyl group represented by the formula

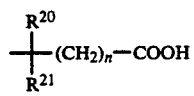

wherein $R^{20}$ and $R^{21}$ independently are hydrogen or $C_{1-3}$ alkyl, or $R^{20}$ and $R^{21}$ taken together with the carbon to which they are bonded form a 3- to 6-membered carbocyclic ring, and n is 0–3.

(d) A number of cephalosporins with heterocycles directly attached to the C-3 position have been reported, for example:

(i) U.S. Pat. No. 4,508,717 issued on Apr. 2, 1985 to Berger et al. discloses, inter alia, cephlosporins of the formula

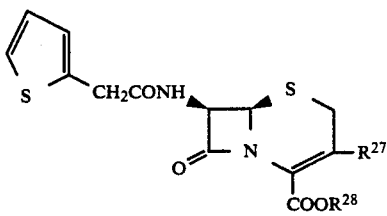

in which $R^{28}$ is hydrogen or diphyenylethyl; and $R^{27}$ is a radical selected from the group

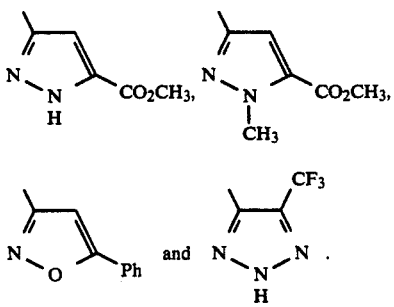

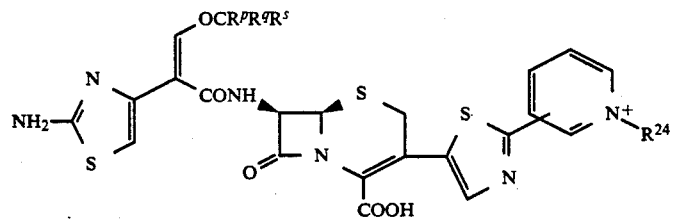

in which $R^{24}$ is methyl, carboxymethyl, carbamoylmethyl, benzyl or allyl radical; $R^p$, $R^q$, and $R^s$ are hydrogen, or alternatively $R^p$ is carboxy and $R^q$ and $R^s$ which are identical or different, are hydrogen atoms or alkyl radicals, or together form an alkylene radical;

(ii) U.S. Pat. No. 4,496,560 issued on Jan. 29, 1985 to Farge relates, inter alia, to compounds of the formula.

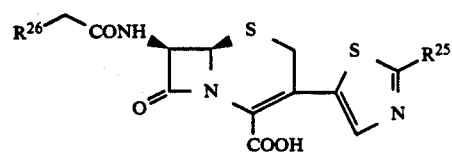

in which $R^{26}$ represents a radical selected from thienyl, furyl, 1,3-dithiol-2-on-4-yl, phenyl, p-hydroxyphenyl, phenoxy and dichlorophenylthio; and $R^{25}$ is hydrogen, phenyl, alkylthio, alkylamino, etc.

(iii) Fahey et al. in the *Journal of Medicinal Chemistry*, 19, 4, p 562 (1976) disclose cephalosporins of the formula (iv) Sugawara et al. in *Chem. Pharm. Bull.*, 28, 7, p 2116 (1980) disclose, inter alia, compounds of formula in which $R^{29}$ equals dimethylamino, 1-morpholino, methyl, phenyl, acetylamino, N-methyl-N-acetylamino and methylamino; and $R^{28}$ is hydrogen or diphenylmethyl.

(v) More recently, at the 200th American Chemical Society meeting held in Washington D.C., Aug. 26–31, 1990, Hornback et al. have disclosed, inter alia, compounds of formula IV'

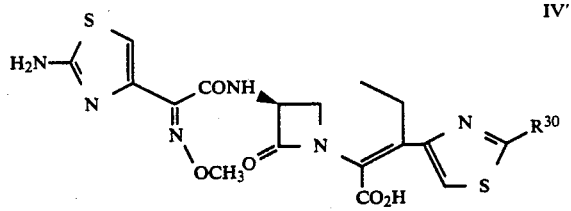

in which R³⁰ is a radical selected from the group

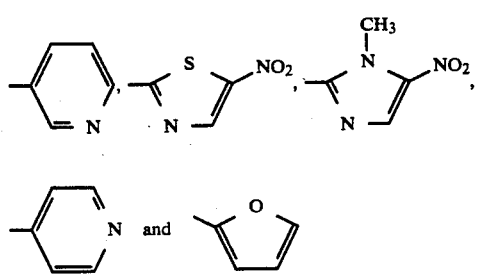

(e) Compounds of formula III, in which X is S or CH₂; and R⁹ and R⁸ are amino and carboxy protecting groups, respectively, have already been described as useful intermediates leading to a variety of cephalosporin related antibiotics. The synthesis of formula III compounds, wherein X is sulfur, has been disclosed by Farina et al. in *The Journal of Organic Chemistry*, 54, 20, p. 4963 (1989). European Patent Application No. 211,540 published on Feb. 25, 1987 discloses the optically active form of 1-carbacephalosporins of formula III. Furthermore, Hatanaka et al. in *Tetrahedron Letters*, 24, 44, p. 4837 (1983) disclose the synthesis of a racemic C-3 hydroxyl 1-carbacephalosporin of formula II, a precursor to a corresponding racemic triflate of formula III.

The utility of compounds of formula III has been demonstrated by Farina et al., in *Tetrahedron Letters*, 29, 47, p 6043 (1988), and Cook et al., in *The Journal of Organic Chemistry*, 54, p. 5828 (1989), wherein the authors took tri-n-butylstannes, n-Bu₃SnR⁷, in the

SCHEME I

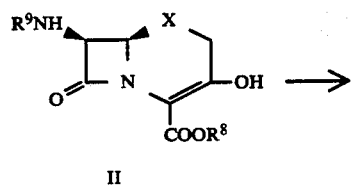

II

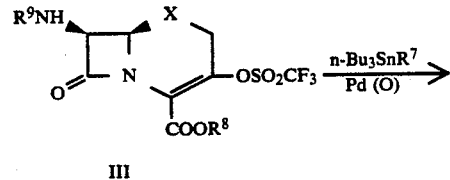

III

-continued
SCHEME I

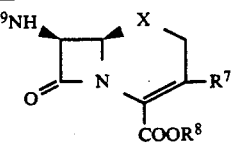

IV presence of a palladium (0) catalyst to transfer a variety of R⁷ radicals to the C-3 positions of compounds of formula III (Scheme I). Examples of R⁷ radicals include alkyl, alkenyl, alkynyl, and aryl.

SUMMARY OF INVENTION

This invention relates to novel compounds of formula I

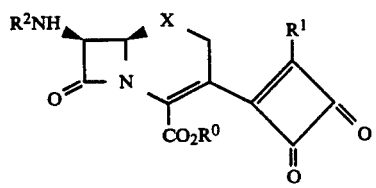

wherein

X is sulfur or CH₂;

R¹ is hydrogen, hydroxy, amino, $C_{1-6}$ alkyl, $C_{2-6}$ alkenyl, $C_{2-6}$ alkynyl, phenyl optionally substituted with one to three $C_{1-6}$ alkyl, $C_{1-6}$ alkyloxy or hydroxy, $C_{1-6}$ alkylthio, phenylthio optionally substituted with one to three $C_{1-6}$ alkyl or $C_{1-6}$ alkyloxy on the phenyl ring, phenylmethyloxy optionally substituted with one to three $C_{1-6}$ alkyl or $C_{1-6}$ alkyloxy on the phenyl ring, 1-morpholino, $C_{1-6}$ alkyloxy, $C_{2-6}$ alkenylmethyloxy, $C_{3-6}$ alkynylmethyloxy, $C_{1-6}$ alkylamino, $C_{1-6}$ dialkylamino or a radical selected from the group consisting of

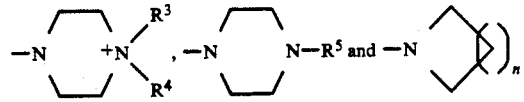

in which n is 0 to 3, R⁵ is $C_{1-6}$ alkyl or hydrogen, and R³ and R⁴ are independently $C_{1-6}$ alkyl;

R² is hydrogen, a conventional amino protecting group or an acyl group;

Rᵒ is hydrogen or a conventional carboxy protecting group, or —CO₂Rᵒ taken together forms a physiologically hydrolyzable ester; or pharmaceutically acceptable salts or solvates thereof.

Representative compounds of this invention were selected for testing and were shown to display potent antimicrobial activity. Thus, in another aspect, the present invention is concerned with pharmaceutical compositions comprising formula I compounds and to methods of treatment comprising administering said compounds or pharmaceutical compositions thereof.

DETAILED DESCRIPTION OF INVENTION

In formula I, when R² is an acyl group as distinguished from a conventional amino protecting group, said acyl group is selected from the preferably pharmacologically active C-7 or C-6 acyl side chains found in the respective cephalosporin or penicillin antibiotic art. Preferable acyl group is that from the cephalosporin art. A recent review by Durckheimer et al., "Recent Developments in the Field of Cephem Antibiotics", *Advances in Drug Research*, 17, pp 16–234 (1988), offers a comprehensive overview of cephalosporin antibiotics.

When the acyl group $R^2$ is represented by a radical $R^aCO—$, more preferred $R^a$ is hydrogen;

$C_{1-6}$ alkyl, $C_{1-6}$ alkyl substituted by cyano, carboxy, halogen, amino, $C_{1-4}$ alkoxy, $C_{1-4}$ alkylthio, or trifluoromethylthio;

a phenyl or substituted phenyl group represented by the formula

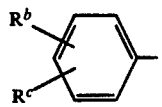

wherein $R^b$ and $R^c$ independently are hydrogen, halogen, hydroxy, $C_{1-4}$ alkoxy, $C_{1-4}$ alkyl, $C_{1-4}$ alkylthio, amino, mono- or di($C_{1-4}$ alkyl)amino, $C_{1-4}$ alkanoylamino, $C_{1-4}$ alkylsulfonylamino, carboxy, carbamoyl, hydroxymethyl, aminomethyl, or carboxymethyl;

a group presented by the formula

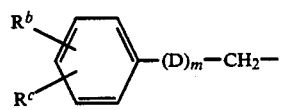

wherein $R^b$ and $R^c$ have the same meanings as defined above, D is oxygen or sulfur, and m is 0 or 1;

a heteroarylmethyl group represented by the formula

wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-4}$ alkyl, $C_{1-4}$ alkoxy, $C_{1-4}$ alkylsulfonylamino;

a substituted methyl group represented by the formula

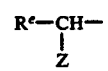

wherein $R^e$ is cyclohex-1,4-dienyl, or a phenyl group or substituted phenyl group

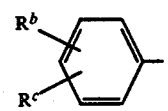

wherein $R^b$ and $R^c$ have the above defined meanings, or $R^e$ is $R^d$ as defined above, and Z is hydroxy, $C_{1-4}$ alkanoyloxy, carboxy, sulfo, or amino;

a keto group or an oximino-substituted group represented by the formulae

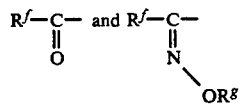

wherein $R^f$ is $R^d$ or $R^e$ as defined above and $R^g$ is hydrogen, $C_{1-6}$ alkyl, cyclic $C_{3-6}$ alkyl or a radical selected from the formulae

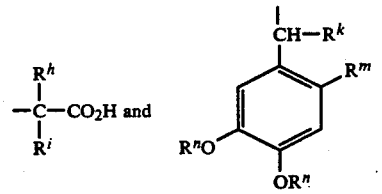

in which $R^h$ and $R^i$ independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen or carboxy, with the proviso that both cannot be the same, and $R^n$ is hydrogen or acetyl; or an alkylidene group of the formulae

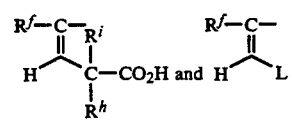

in which L is halogen or $CF_3$, and $R^f$, $R^i$ and $R^h$ are as defined above.

Even more preferred $R^a$ group is a radical selected from the group

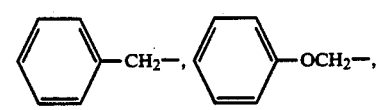

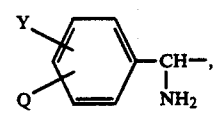

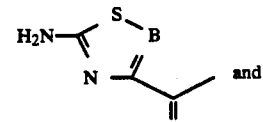

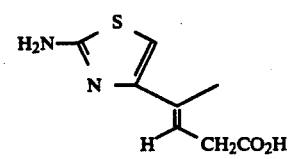

wherein B is nitrogen or CH; Y and Q are independently hydrogen, hydroxy or halogen; and $R^g$ has the above defined meaning.

The most preferred $R^a$ group is a radical of the formulae

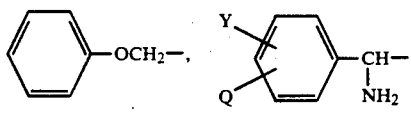

and

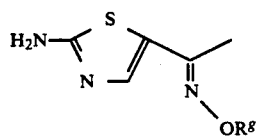

in which $R^9$ is hydrogen, $C_{1-6}$ alkyl, cyclic $C_{3-6}$ alkyl or a radical of the formula

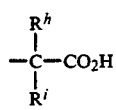

in which $R^h$ and $R^i$ are as defined above.

In the above definition of the compounds represented by formula I, $C_{1-6}$ alkyl refers to straight and branched chain alkyl groups such as methyl, ethyl, n-propyl, isopropyl, n-butyl, t-butyl, n-pentyl, n-hexyl, 3-methylpentyl, and like alkyl groups; $C_{1-6}$ dialkylamino refers to disubstituted amino groups in which the two substituents may be the same or different, such as dimethylamino, N-ethyl-N-methylamino, N-ethyl-N-propylamino, diethylamino, and like groups; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, and the like groups; $C_{2-6}$ alkynyl refers to straight or branched chain alkynyl groups such as ethynyl, 1-propynyl, propargyl, and the like groups; phenyl substituted with one to three $C_{1-6}$ alkyl, $C_{1-6}$ alkyloxy or hydroxy refers to groups such as 4-methylphenyl, 4-methoxyphenyl, 4-hydroxyphenyl, 3,4-dihydroxyphenyl, 3-methyl-4-hydroxyphenyl, 2-methyl-3-hydroxy-4-methoxyphenyl, and the like groups in which the total number of substituents on the phenyl ring does not exceed three; $C_{1-6}$ alkyl substituted by cyano refers to cyanomethyl, cyanoethyl, 4-cyanobutyl, and the like; $C_{1-6}$ alkyl substituted by carboxy refers to such groups as carboxymethyl, 2-carboxyethyl, 2-carboxypropyl, 4-carboxybutyl, 5-carboxypentyl, and the like; halogen refers to fluoro, chloro, bromo, or iodo, thus, $C_{1-6}$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_{1-6}$ alkyl substituted by amino refers to such groups as 2-aminoethyl, aminomethyl, 3-aminopropyl, and 4 aminobutyl; $C_{1-6}$ alkyl substituted by $C_{1-4}$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxy-pentyl, 6-methoxyhexyl, and like group; $C_{1-6}$ alkyl substituted by $C_{1-4}$ alkythio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_{1-6}$ alkyl substituted by trifluoromethyl is exemplified by 2,2,2-trifluoroethyl, 3,3,3-trifluoropropyl, 4,4,4-trifluorobutyl, and the like; and $C_{1-6}$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_{1-6}$ alkyl substituted groups; cyclic $C_{3-6}$ alkyl group refers to groups such as cyclopropyl, cyclobutyl, cyclopentyl, cyclohexyl, cyclopropylmethyl, cyclopropylethyl, cyclopropylpropyl, cylcobutylmethyl, cyclobutylethyl, cyclopentylmethyl, etc.

When $R^a$ is a substituted phenyl group wherein the substituent(s) are represented by $R^b$ and $R^o$, examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylaminophenyl such as 2-acetylaminophenyl, 4-acetylaminophenyl, 3-propionylaminophenyl, and 4-butyrylaminophenyl; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl, and 3-ethylsulfonylaminophenyl; carboxyphenyl such as 2-,3-, or 4-carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4 dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-methoxy-3-hydroxyphenyl, 4-methylsulfonylamino-2-carboxyphenyl, 4-amino-3-chlorophenyl, and 2-carboxymethyl-4-hydroxyphenyl.

Examples of $R^aCO$-groups wherein $R^a$ is a group represented by the formula

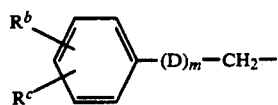

with m equals 0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m equals 1 and D equals oxygen, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m equals 1 and D equals sulfur, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^d$-$CH_2CO$ groups wherein $R^d$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups optionally substituted by amino, $C_{1-4}$ alkylsulfonylamino, hydroxy, halogen, $C_{1-4}$ alkyl or $C_{1-4}$ alkoxy groups.

Examples of $R^aCO$ -groups wherein $R^a$ is a substituted methyl group represented by the formula $R^e$-CH(Z)- and Z is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl; 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2(benzofur-2-yl)acetyl.

Examples of $R^aCO$ acyl groups in which $R^a$ is a keto group or an oximino-substituted group represented by the formulae

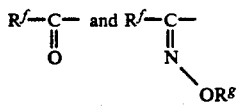

are the keto groups such as 2-oxo-2-phenylacetyl, 2-oxo-2-(2-thienyl)acetyl, and 2-oxo-2-(2-aminothiazol-4-yl)acetyl; and the oximino-substituted groups such as 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)-iminoacetyl, 2-(5-amino-1,2,4-thiadiazol-3-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoyl-prop-2-yl)oxyiminoacetyl, and 2-(5-amino-1,3,4-thiadiazol-2-yl)-2-methoxyiminoacetyl.

Examples of $R^aCO$ acyl groups wherein $R^a$ is an alkylidene represented by the formulae

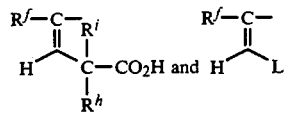

are 2-(2-aminothiazol-4-yl)-2-(2,2-dimethyl-2-carboxyethylidene)acetyl, 2-(2-aminothiazol-4-yl)-2-(2-trifluoroethylidene)acetyl, and the like.

Conventional carboxy-protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, diphenylmethyl (benzyhydryl), 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl $C_{1-6}$ alkyl, ring substituted phenyl $C_{1-6}$ alkyl, e.g., benzyl, 4-methoxybenzyl, 4-nitrobenzyl (p-nitrobenzyl), 2-nitrobenzyl (o-nitrobenzyl), and triphenylmethyl (trityl), methoxymethyl, 2,2,2-trichloroethoxycarbonyl, benzyloxymethyl, $C_{1-6}$ alkanoyloxy $C_{1-6}$ alkyl such as acetoxymethyl, propionyloxymethyl, $C_{2-6}$ alkenyl such as vinyl and allyl. Other suitable carboxy protecting groups well known in the art which have not been disclosed above can be found in "Protective Groups in Organic Synthesis", Theodora W. Greene (John Wiley & Sons, 1981), Chapter 5 incorporated herein by reference. Particularly advantageous carboxy protecting groups are benzyl, p-nitrobenzyl, o-nitrobenzyl, 2,4-dimethoxybenzyl, 4-methoxybenzyl, allyl, substituted allyl, t-butyl or diphenylmethyl (DMP).

Conventional amino protecting groups are also well-known to those skilled in the art and have reference to groups commonly employed in protecting or blocking the amino functional group during a reaction step and which can be split off subsequently without destroying or substantially destroying the remaining portion of the molecule. Examples include vinyl, allyl, t-butoxycarbonyl, benzyl, benzyloxycarbonyl, 2-nitrobenzyl, 4-nitrobenzyl, 2-nitrobenzyloxylcarbonyl, formyl, benzoyl, acetyl, ethylcarbonyl, chloroacetyl, trichloroacetyl, trifluoroacetyl, methyloxycarbonyl, allyloxycarbonyl, trimethylsilyl, triethylsilyl, triphenylsilyl, t-butyl-dimethylsilyl, methyldiphenylsilyl, 2,4-dimethoxybenzyl, 2,4-dimethoxybenzyloxycarbonyl, 4-methoxybenzyl, 4-(methoxymethyloxy)phenyl, bis-(4-methoxyphenyl)-methyl, t-butoxycarbonylmethyl, allyoxycarbonylmethyl, methoxymethyl, methylthiomethyl, methoxyethoxymethyl, [2-(trimethylsilyl)ethoxy]methyl or 2-(methylthiomethoxy)ethoxycarbonyl. In general, amino protecting groups which are readily removed under acid conditions or catalytic hydrogenolysis are preferred, e.g. t-butoxycarbonyl, benzyloxycarbonyl and triphenylmethyl. Other suitable amino protecting groups well known to those skilled in the art can be found in "Protective Groups in Organic Synthesis", Theodora W. Greene (John Wiley & Sons, 1981), Chapter 7, incorporated herein by reference.

The structural formula I as drawn herein is believed to best represent the structures of compounds of the present invention. However, some compounds within the scope of the invention may exit as other tautomeric forms, in which hydrogen atoms are transposed to other parts of the molecules and the chemical bonds between the atoms of the molecules are consequently rearranged. For example, when a compound of formula I has R¹ as the radical

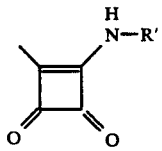

in which R' is $C_{1-6}$ alkyl, it is well understood that such radical can equally be drawn as

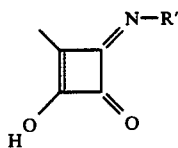

The present invention includes all tautomeric forms, insofar as they may exist.

The compounds of formula I have several asymmetric carbon atoms and can thus exit in several stereochemical forms. This invention covers the mixtures of isomers and the individual stereoisomers. Preferred isomers of formula I compounds are those as drawn, for example, where X is $CH_2$, those having the 6R, 7S configuration are preferred. Further, when $R^a$ is of the radical

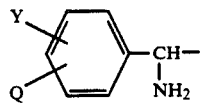

the "D" configuration at the benzylic carbon is preferred.

Besides the tautomeric and asysmmetric stereoisomerisms which may exit in compounds of formula I, there can be "syn" (Z) and "anti" (E) stereoisomerism arising from different orientations of substituent(s) on a double bond. Unless otherwise explicitly stated, the present invention comprises both the pure and the mixture of "syn" and "anti" isomers. For example, when a compound of formula I has an oximino radical substituted with an aminothiazolyl or aminothiadiazolyl ring represented by the formula

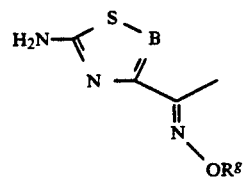

as Ra, and in which B and $R^9$ are as previously defined, the imino group has either the "syn" (Z) or "anti" (E) configuration. The radical is drawn as the "syn" isomer. This invention comprises compounds of formula I with the oximino radical with at least 90% of the "syn" isomer. Preferably the above-mentioned radicals are "syn" isomers which are essentially free of the corresponding "anti" isomers.

Also included within the scope of the invention are the non-toxic pharmaceutically acceptable salts, physiologically hydrolyzable esters or solvates of compounds of formula I.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, benzyl, 4-methoxybenzyl, indanyl, phthalidyl, methoxymethyl, $C_{1-6}$ alkanoyloxy $C_{1-6}$ alkyl, e.g. acetoxymethyl, pivaloyloxymethyl or propionyloxymethyl, $C_{1-6}$ alkoxycarbonyloxy $C_{1-6}$ alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other physiologically hydrolyzable esters known and used in the penicillin and cephalosporin arts. Such esters are prepared by conventional techniques known in the art.

The pharmaceutically acceptable acid addition salts of formula I compounds are those in which anion does not contribute significantly to the toxicity of the salt and are compatible with the customary pharmaceutical vehicles and adapted for oral or parenteral administration. The pharmaceutically acceptable acid addition salts include the salts of compounds of formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, isethionic acid, p-tolenesulfonic acid and other acids known and used in the penicillin and cephalosporin arts. Preparation of these salts is carried out by conventional techniques involving reaction of compounds of formula I with the acid in a substantially equivalent amount.

Compounds of formula I could also form pharmaceutically acceptable metal and amine salts in which the cation does not contribute significantly to the toxicity or biological activity of the salt. These salts are also part of the present invention. Suitable metal salts include the sodium, potassium, calcium, barium, zinc and aluminum salts. The sodium or potassium salts are preferred. Amine salts prepared from amines used, for instance, with benzyl penicillin which are capable of forming stable salts with the acidic carboxy group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine and dicyclohexylamine.

Compounds of formula I exhibit high antibacterial activity against various Gram-positive and Gram-negative bacteria, and are useful in the treatment of bacterial infections in animals, including man. Compounds of formula I may be formulated for parenteral use in a conventional manner utilizing known pharmaceutical carriers and excipients, and may be presented in unit dosage form or in multidosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. Compounds of formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of formula I. The dosage of the compounds of formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

Compounds of the present invention may be made through the steps shown in Scheme II. In the scheme X, $R^1$, $R^2$, $R^8$, and $R^9$ are as previously defined.

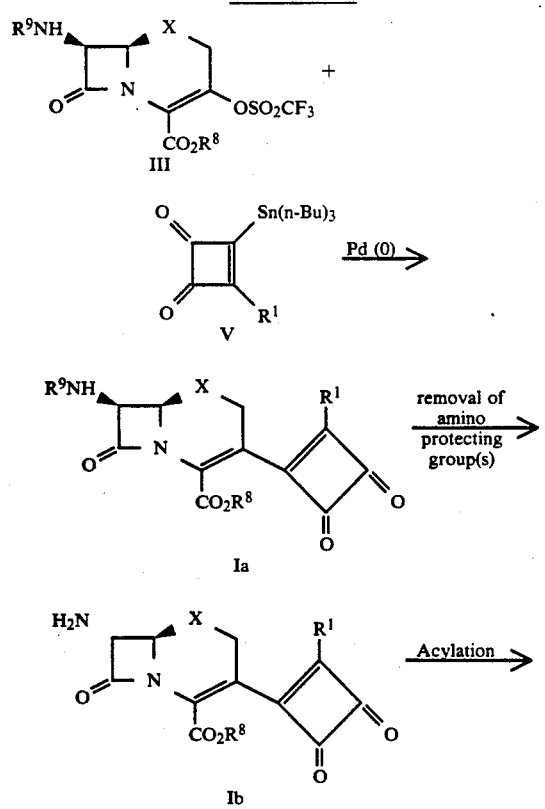

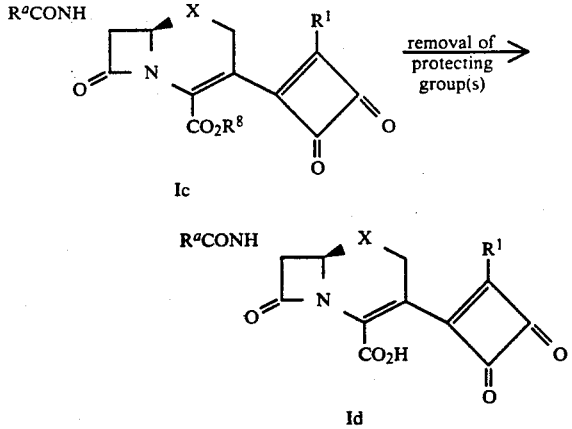

The synthesis of tri-n-butylstannylcyclobutenediones of general formula V was a topic of a recent doctoral thesis by Fengel which was catalogued on Mar. 28, 1990 under QD 1.5F44 in the library of Emory University, Atlanta, Ga. The synthesis of the tri-n-butylstannylcyclobutenediones in which $R^1$ is amino, $C_{1-6}$ alkylthio, phenylthio optionally substituted with one to three $C_{1-6}$ alkyl or $C_{1-6}$ alkyloxy on the phenyl ring, phenylmethyloxy optionally substituted with one to three $C_{1-6}$ alkyl or $C_{1-6}$ alkyloxy on the phenyl ring, 1-morpholino, $C_{1-6}$ alkyloxy, $C_{2-6}$ alkenylmethyloxy, $C_{3-6}$ alkynylmethyloxy, $C_{1-6}$ alkylamino, $C_{1-6}$ dialkylamino or a radical selected from the group consisting of

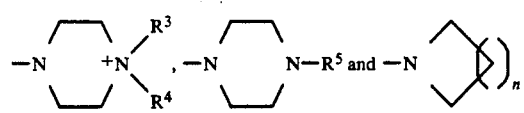

in which n, $R^3$, $R^4$, and $R^5$ are as defined above can be made according to a general method illustrated in Scheme III.

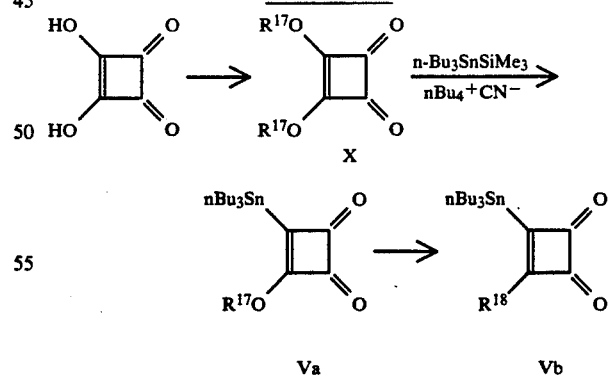

Typically, squaric acid is converted to squaric acid esters of formula X, in which $R^{17}$ is $C_{1-6}$ alkyl, $C_{2-6}$ alkenylmethyloxy, $C_{3-6}$ alkynylmethyloxy, phenylmethyl optionally substituted with one to three $C_{1-6}$ alkyl or $C_{1-6}$ alkyloxy on the phenyl ring by a general method described by Maahs in Liebigs *Ann. Chem.*, 686, p 55 (1965), by Eckehad et al., in *Chemische Berichete*, 113, 1, p. 1 (1980), and by Cohen et al., in the *Journal of*

*the American Chemical Society,* 88, p 1533 (1966). Subsequently, a squaric acid ester of formula X is treated with n-Bu₃SnSiMe₃ and a catalytic amount of n-Bu₄⁺CN⁻ to afford a tri-n-butylstannylcyclobutenedione of formula Va. The reaction is effected in an inert solvent, typically in THF, and at low temperature, preferably between 0° C. and −50° C. A compound of formula Va may subsequently be reacted with NH₃, morpholine, $C_{1-6}$ alkylthiol, phenylthiol optionally substituted with $C_{1-6}$ alkyl or $C_{1-6}$ alkyloxy on the phenyl ring, $C_{1-6}$ alkylamine, $C_{1-6}$ dialkylamine or an amine selected from the group

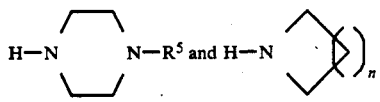

to make additional compounds within the scope of formula V. A compound of formula Va may also be treated with an amine of the formula

to afford a compound of formula Vb in which $R^{18}$ is the radical

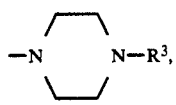

and the resulting compound Vb is alkylated with $R^4$-P, in which P is a leaving group, typically chloro, bromo or iodo, to afford additional compounds of formula V.

The synthesis of compounds of formula V in which $R^1$ is hydrogen, $C_{1-6}$ $C_{2-6}$ alkenyl, $C_{2-6}$ alkynyl, phenyl optionally substituted with one to three $C_{1-6}$ alkyl, $C_{1-6}$ alkyloxy or hydroxy can be carried out as shown in Scheme IV. In the scheme, a squaric acid ester of formula X, whose synthesis has been described above, is reacted with $C_{1-6}$ alkyllithium , $C_{2-6}$ alkenyllithium, $C_{2-6}$ alkynyllithium , phenyllithium optionally substituted with one to three $C_{1-6}$ alkyl, $C_{1-6}$ alkyloxy, or hydroxy on the phenyl ring, or a reducing agent such as diisobutylaluminum hydride, lithium tri-t-butoxyaluminum hydride, and the like, to afford an alcohol of formula XI. In formula XI, $R^{19}$ is hydrogen, $C_{1-6}$ alkyl, $C_{2-6}$ alkenyl, $C_{2-6}$ alkynyl, phenyl optionally substituted with one to three $C_{1-6}$ alkyl, $C_{1-6}$ alkyloxy, or hydroxy protected with aryl hydroxy protecting group(s). In this step, it should be

SCHEME IV

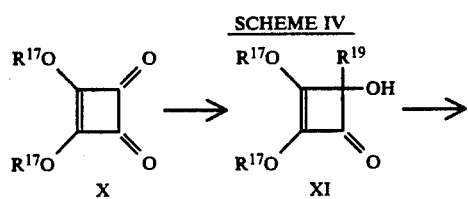

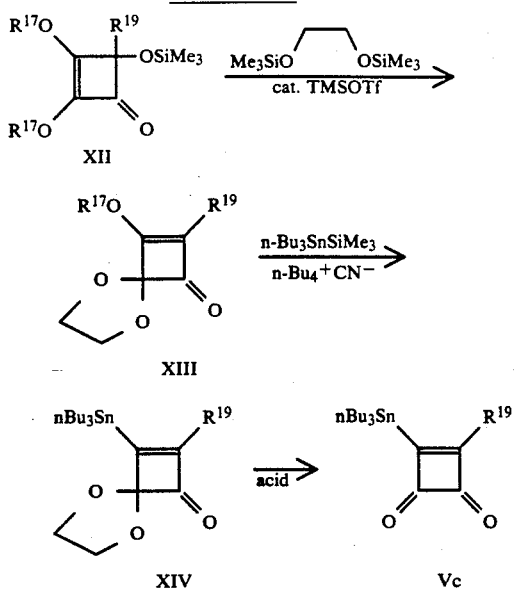

understood that phenyllithium with one to three hydroxy substituents needs to have the hydroxy groups protected with conventional aromatic hydroxy protecting groups. Conventional aromatic hydroxy protecting groups includes groups such as methyl, methoxyethoxymethyl, methylthiomethyl, tetrahydropyranyl, cyclopropylmethyl, allyl, isopropyl, t-butyl, benzyl, o-nitrobenzyl, 4-picolyl, 9-anthrylmethyl, trimethylsilyl, t-butyldimethylsilyl, acetyl, pivaloyl, benzoyl, aryl 9-fluorenecarbonyl, methyloxycarbonyl, 2,2,2-trichloroethyloxycarbonyl, vinyloxycarbonyl, benzylcarbonyl, methylsulfonyl, and the like groups. Particularly useful protecting groups for two hydroxy groups on adjacent phenyl carbon atoms (i.e. catechols) are groups such as methylene, cyclohexylidene, isopropylidene, diphenylmethylene, and the like groups. Other commonly used aromatic hydroxy protecting groups are disclosed in "Protecting Groups in Organic Synthesis," Tehodora W. Greene (John Wiley & Sons, 1981), Chapter 3.

The transformation of a compound of formula XI to a trimethylsilylether of formula XII can most conveniently be carried out by treating the former with trimethylsilylchloride and an organic base such as triethylamine. The silyation of an alcohol group is well known in the art. The trimethylsilyl ether XII thus obtained is subsequently treated with ethylene glycol bistrimethylsilyl ether in the presence of a catalytic amount of (c.a. 0.1%) trimethylsilyl triflate in an inert solvent, typically tetrahydrofuran, to afford a cyclobutenedione monoacetal of formula XIII. Similar to a step in Scheme II above, a cyclobutenedione monoacetal XIII is treated with n-Bu₃SnSiMe₃ and a catalytic amount n-Bu₄⁺CN⁻ to yield a 3-tri-n-butylstannyl-4-R¹⁹-3-cyclobutene-1,2-dione-2-ethylene acetal of formula XIV. By mild acid hydrolysis of the ethylene acetal group, more compounds within the scope of compounds of formula V are obtained.

The coupling of a compound of formula III with a compound of formula V can be effected using an organo-palladium palladium (0) and tri(2-furyl)phosphine as catalysts. The most preferred palladium (0) catalyst is bis(dibenzylideneacetonyl)-palladium (0). Further, an additional presence of zinc chloride as a co-catalyst provides an even better yield. The coupling can be effected in an inert solvent such as THF or acetonitrile, but the best result can be obtained using N-methylpyrrolidinone as solvent.

The N-acylation with a $R^aCO$ radical to a compound of formula Ib can be accomplished by any one of the standard, well-known acylating methods used for the N-acylation of cephalosporin and penicillin nuclei. For example, a nucleus of formula Ib is coupled with an acid $R^aCOOH$ in the presence of a dehydrating agent such as dicyclohexylcarbodiimide, 1-ethoxycarbonyl-2-ethoxy-1,2-dihydroquinoline (EEDQ) or any other suitable reagents which appear in *Synthesis*, pp 453–463 (1972). Alternatively a carboxylic acid can be converted to a reactive derivative of the carboxy group and the reactive derivative used in the N-acyation. Reactive derivatives of the carboxy group that can be used are acid halides, acid azides, mixed acid anyhydrides, acitve esters such as those formed with ethyl chloroformate and isobutyl chloroformate; phenylcarbamates; N-hydroxyimides such as formed with N-hydroxysuccinimide and N-hydroxyphthalimide; and those formed with hydroxybenzotriazole (HBT) and 4-methyltetrazole-5-thione; and like active carboxy derivates. During the N-acylation any free hydroxy, amino or carboxy groups present in the carboxylic acid $R^aCOOH$ are desirably protected with conventional protecting groups. Similar to the definition of conventional amino and carboxy protecting groups, conventional hydroxy protecting groups represents a group commonly employed in protecting the hydroxy group during a reation step and which can be split off subsequently without destroying or substantially destroying the remaining portion of the molecule. Examples include trimethylsilyl, triethylsilyl, triisopropylsilyl, t-butyl-dimethylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, t-butyloxycarbonyl, allyloxycarbonyl, 4-methoxybenzylcarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl or benzoyl.

In a compound of formula Ic, when $R^1$ is benzyloxy, the compound can be treated with aluminum chloride in a nitromethane/methylene chloride solution containing anisole to convert $R^1$ group into hydroxy. In the same molecule, when carboxyl group $R^8$ is diphenylmethyl, the same reagent deprotects the carboxy group simultaneously.

DESCRIPTION OF SPECIFIC EMBODIMENTS

The specific examples which follow illustrate the synthesis of representative compounds of the instant invention and are not construed as limiting the invention in sphere or scope. The methods may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethysulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value. Celite is a registered trademark of the Johns-Manville Products Corporation for diatomaceous earth.

The abbreviations used herein are conventional abbreviations widely employed in the art. Some of which are:

| | |
|---|---|
| FAB | Fast Atom Bombardment |
| psi | pound per square inch |
| DMSO | dimethyl sulfoxide |
| Boc | t-butoxycarbonyl |
| DPM | diphenylmethyl |
| Ph | phenyl |
| NPM | N-methyl-2-pyrrolidionone |
| Cbz | benzyloxycarbonyl |
| pTSOH | p-toluenesulfonic acid |
| NOBA | p-nitrobenzylalcohol |
| TFA | trifluoroacetic acid |
| HPLPLC | high performance low pressure liquid chromatography |
| Triton B | Benzyltrimethylammonium hydroxide, 40% solution in methanol |
| tBu | t-butyl |
| HPLC | High pressure liquid chromatography |

EXAMPLE 1

Diphenylmethyl 7-(t-butoxycarbonylamino)-3-(3,4-dioxo-2-(2-propoxy)-1-cyclobutenyl)-3-cephem-4-carboxylate Ia$_1$ A solution of diphenylmethyl 7-(t-butyloxycarbonylamino)-3-trifluoromethylsulfonyloxy-3-cephem-4-carboxylate (307 mg, 0.50 mmol) and 4-(2-propoxy)-3-(tri-n-butylstannyl)cyclobut-3-ene-1,2-dione (236 mg, 0.55 mmol) in N-methyl-2-pyrrolidinone (NMP, 4.5 mL) was degassed with a gentle stream of argon. Tris(2-furyl)phosphine (11.5 mg, 0.050 mmol), zinc chloride (136 mg, 1.0 mmol), and bis(dibenzylidene-acetone) palladium (0) (14.4 mg, 0.025 mmol) were successively added. The mixture was stirred at an oil bath temperature of 60°–65° C. for 0.5 hr and was diluted with ethyl acetate. The resulting solution was sequentially washed with saturated aqueous NH$_4$Cl (3X), H$_2$O, and saturated NaCl and then was dried over Na$_2$SO$_4$. The filtrate was concentrated, and a solution of the residue in acetonitrile was washed with n-pentane (3X). Removal of the acetonitrile left a dark oil which was chromatographed on SiO$_2$ (19 g) with methylene chloride-acetone (97:3) to afford the title compound (228 mg, 75% yield) as a bright yellow solid. Recrystallization from diisopropyl ether gave the analytical sample.

Anal. Calcd for C$_{32}$H$_{32}$N$_2$O$_8$S: C, 63.57; H, 5.34; N, 4.64.
Found: C, 63.17; H, 5.51; N, 4.53.

EXAMPLE 2

In an analogous manner to that described in Example 1, replacement of 4-(2-propoxy)-3-(tri-n-butylstannyl)-cyclobut-3-ene-1,2-dione with 4-benzyloxy-3-(tri-n-butylstannyl)cyclobut-3-ene-1,2-dione, 4-amino-3-(tri-n-butylstannyl)cyclobut-3-ene-1,2-dione, and 4-methyl-3-(tri-n-butylstannyl)cyclobut-3-ene-1,2-dione afforded the respective cephalosporins of formula Ia (wherein $R^9$ = Boc, $R_8$ = DPM):

a. Diphenylmethyl 7-(t-butoxycarbonylamino)-3-(2-benzyloxy-3,4-dioxo-1-cyclobutenyl)-3-cephem-4-carboxylate (Ia$_2$), isolated as a bright yellow solid (50.8% yield).

NMR: (CDCl$_3$, 300 MHz) δ 7.2–7.5 (15H, m), 6.86 (1H, s), 5.69 (1H, dd, J=9 Hz, J=5.4 Hz), 5.45 (1H, d, J=11.4 Hz), 5.17 (2H, overlapping d, J=11.4 Hz, J=9 Hz), 4.95 (1H, d, J=5.4 Hz), 4.09 (1H, d, J=18 Hz), 3.39 (1H, d, J=18 Hz), 1.39 (9H, s).

b. Diphenylmethyl 7-(t-butoxycarbonylamino)-3-(2-amino-3,4-dioxo-1-cyclobutenyl)-3-cephem-4-carboxylate (Ia$_3$), isolated as a buff solid (69% yield).

NMR: (DMSO-D$_6$, 300 MHz) δ 9.03 (1H, s), 8.77 (1H, s,), 8.13 (1H, d, J=9 Hz), 7.2–7.4 (10H, m), 6.71 (1H, s), 5.68 (1H, dd, J=9 Hz, J=5.1 Hz), 5.19 (1H, d, J=5.1 Hz), 3.96 (1H, d, J=18 Hz), 3.62 (1H, d, J=18 Hz), 1.41 (9H, s).

c. Diphenylmethyl 7-(t-butoxycarbonylamino)-3-(3,4-dioxo-2-methyl-1-cyclobutenyl)-3-cephem-4-carboxylate (Ia$_4$), isolated as yellow crystals from acetonitrile.

Anal. Calcd for $C_{30}H_{28}N_2O_7S$: C, 64.28; H, 5.04; N, 5.00.
Found: C, 63.88; H, 5.12; N, 4.99.

EXAMPLE 3

(±)-t-Butyl 7-phenoxyacetamido-3-(3,4-dioxo-2-(2-propoxy)-1-cyclobutenyl)-1-carba(1-dethia)-3-cephem-4-carboxylate (Ia$_5$)

A solution of (±)-t-butyl 7-phenoxyacetamido-3-trifluoromethylsulfonyloxy-1-carba(1-dethia)-3-cephem-4-carboxylate (100 mg, 0.192 mmol) and 4-(2-propoxy)-3-(tri-n-butylstannyl)cyclobut-3-ene-1,2-dione (105 mg, 0.245 mmol) in NMP (1.4 mL) was degassed with a gentle stream of argon. Tris(2-furyl)phosphine (5.7 mg, 0.025 mmol), zinc chloride (67 mg, 0.49 mmol) and bis(dibenzylidene acetone)palladium (0) (7.5 mg, 0.013 mmol) were successively added. The mixture was stirred at an oil bath temperature of 65° C. for 0.5 hr and was diluted with ethyl acetate. The resulting solution was sequentially washed with saturated aqueous NH$_4$Cl (3X), H$_2$O, and saturated aqueous NaCl and then was dried over Na$_2$SO$_4$. The filtrate was concentrated, and a solution of the residue in acetonitrile was washed with n-pentane (3X). Removal of the acetonitrile left a solid which was chromatographed on SiO$_2$ (13 g) with methylene chloride-ethyl acetate (90:10) to afford the title compound, which was crystallized from methylene chloride-hexanes to give yellow crystals (52 mg, 53% yield).

NMR: (CDCl$_3$, 300 MHz) δ 7.25–7.30 (2H, m), 6.97–7.01 (2H, m), 6.84–6.86 (2H, m), 5.41–5.49 (2H, m), 4.50 (2H, s), 3.91–3.95 (1H, m), 2.99–3.05 (1H, m), 2.10–2.21 (1H, m), 1.94–2.04 (1H, m), 1.50 (9H, s), 1.4–1.53 (1H, m), 1.37–1.42 (6H, m).

EXAMPLE 4

(±)-t-Butyl 7-(benzyloxycarbonylamino)-3-(2-amino-3,4-dioxo-1-cyclobutenyl)-1-carba(1-dethia)-3-cephem-4-carboxylate (Ia$_6$)

A solution of (±)-t-butyl 7-(benzyloxycarbonylamino)-3-trifluoromethylsulfonyloxy-1-carba(1-dethia)-3-cephem-4-carboxylate (2.79 g, 5.36 mmols) and 4-amino-3-(tri-n-butylstannyl)cyclobut-3-ene-1,2-dione (2.28 g, 5.9 mmols) in NMP (30 mL) was degassed with a gentle stream of nitrogen. Tris(2-furyl)phosphine (123 mg, 0.53 mmol), zinc chloride (1.46 g, 10.7 mmols), and tris(dibenzylidene acetone)dipalladium (0) (247 mg, 0.27 mmol) were successively added. Stirring was continued at 22° C. for 0.33 hr and then for 0.25 hr at an oil bath temperature of 65° C. The mixture was poured into ethyl acetate. The solution was washed with saturated aqueous ammonium chloride and then with saturated sodium chloride. The solution was dried over Na$_2$SO$_4$, and the filtrate was concentrated to dryness. A solution of the residue in acetonitrile was washed twice with n-pentane. Partial concentration of the acetonitrile afforded a crystalline solid which was recrystallized a second time from acetonitrile with charcoal treatment to afford yellow crystals of the title compound (1.92 g, 76% yield).

NMR: (DMSO-D$_6$, 300 MHz) δ 8.85 (1H, s), 8.52 (1H, s), 8.13 (1H, d), 7.25–7.36 (5H, m), 5.26 (1H, m), 5.04 (2H, ABq), 3.82 (1H, m), 2.84–2.92 (1H, m), 2.09–2.21 (1H, m), 1.77–1.9 (1H, m), 1.52–1.7 (1H, m), 1.36 (9H, s).

Anal. Calcd for $C_{24}H_{25}N_3O_7$: C, 61.67; H, 5.40; N, 8.99.
Found: C, 61.74; H, 5.36; N, 9.04.

EXAMPLE 5 t-Butyl (6R,7S)-7-(benzyloxycarbonylamino)-3-(2-amino-3,4-dioxo-1-cyclobutenyl)-1-carba(1-dethia)-3-cephem-4-carboxylate (Ia$_6$').

In a manner analogous to that described in Example 4, t-butyl (6R,7S)-7-(benzyloxycarbonylamino)-3-trifluoromethylsulfonyloxy-1-carba(1-dethia)-3-cephem-4-carboxylate (1.5 g) was cross-coupled with 4-amino-3-(tri-n-butylstannyl)cyclobut-3-ene-1,2-dione (1.1 g) to afford the title compound (1.3 g).

EXAMPLE 6

Diphenylmethyl 7-amino-3-(2-amino-3,4-dioxo-1-cyclobutenyl)-3-cephem-4-carboxylate (Ib$_1$)

Diphenylmethyl 7-(t-butoxycarbonylamino)-3-(2-amino-3,4-dioxo-1-cyclobutenyl)-3-cephem-4-carboxylate (400 mg, 0.712 mmol) was added to a stirred solution of p-toluenesulfonic acid monohydrate (272 mg, 1.43 mmols) in acetonitrile (1.6 mL). Stirring was continued for 0.5 hr at 22° C., at which time additional acetonitrile (1mL) and H$_2$O (2 drops) were added. Stirring was continued for an additional 0.5 hr at 22° C. and then for 0.33 hr at a water bath temperature of 35²⁰–40° C. The solution was applied to a Michel-Miller HPLPLC column (22×300 mm, purchased from Ace Glass) containing Partisil Prep 40 ODS-3 (purchased from Whatman Chemical Separation Inc., Clifton, N.J.). The column was eluted with a mixture of 80% acetonitrile-20% H$_2$O (50%) and 0.05M (pH 6.5) ammonium phosphate (50%). The appropriate fractions were combined and acetonitrile was removed on a rotary evaporator. The resulting mixture was extracted with ethyl acetate (3X). The combined extracts were washed (saturated aqueous NaCl), dried (MgSO$_4$), and partially concentrated. Dilution with n-heptane precipitated the title compound as a yellow powder (93.6 mg, 28% yield). Analytical HPLC indicated a purity of 97 area percent.

NMR: (DMSO-D$_6$, 300 MHz) δ 8.98 (1H, s), 8.72 (1H, s), 7.2–7.4 (10H, m), 6.69 (1H, s), 5.10 (1H, d), 4.94 (1H, d), 3.92 (1H, d, J=18 Hz), 3.59 (1H, d, J=18 Hz).

HPLC: (retention time=2.46 minutes). Waters C$_{18}$ radial pak cartridge. 2.0 mL/min of 30% pump A (0.05M, pH 6.5 ammonium phosphate) and 70% pump B (80% acetonitrile-20% H$_2$O). Detect at 254 nm.

EXAMPLE 7

Diphenylmethyl 7-amino-3-[3,4-dioxo-2-(2-propoxy)-1-cyclobutenyl]-3-cephem-4-carboxylate (Ib$_2$)

A solution of diphenylmethyl 7-(t-butoxycarbonylamino)-3-(3,4-dioxo-2-(2-propoxy)-1-cyclobutenyl)-3-cephem-4-carboxylate (300 mg, 0.496 mmol) and p-toluenesulfonic acid monohydrate (189 mg, 0.992 mmol) in acetonitrile (1.5 mL) was stirred for 1 hr at 22° C. The solution was applied to the Michel-Miller HPLPLC column. The column was eluted with acetonitrile-H$_2$O (45:55, v/v) to remove the toluene-sulfonic acid and then with acetonitrile-H$_2$O (70:30, v/v) to elute the deblocked amine. The acetonitrile was removed on a rotary evaporator and the resulting mixture extracted twice with ethyl acetate. The combined extracts were washed (saturated NaCl), dried (Na$_2$SO$_4$), and concentrated to leave the title compound (146 mg, 58% yield) as a yellow powder.

NMR: (CDCl$_3$, 300 MHz) δ 7.2–7.5 (10H, m), 6.9 (1H, s), 5.18 (1H, m), 4.95 (1H, d), 4.82 (1H, d), 3.98 (1H, d), 3.4 (1H, d), 1.67 (1H, broad s), 1.28 (6H, m).

EXAMPLE 8

Diphenylmethyl 7-amino-3-(3,4-dioxo-2-methyl-1-cyclobutenyl)-3-cephem-4-carboxylate (Ib$_3$)

A solution of diphenylmethyl 7-(t-butoxycarbonylamino)-3-(3,4-dioxo-2-methyl-1 cyclobutenyl)-3-cephem-4-carboxylate (100 mg, 0.178 mmol) and p-toluenesulfonic acid monohydrate (pTSOH.H$_2$O, 68 mg, 0.357 mmol) in acetonitrile (0.5 mL) was stirred for 1 hr at 22° C. when additional pTSOH.H$_2$O (34 mg, 0.178 mmol) was added. Stirring was continued for an additional 0.5 hr when the mixture was diluted with ethyl acetate. The solution was sequentially washed with dilute aqueous NaHCO$_3$, H$_2$O, and saturated NaCl. The solution was dried (Na$_2$SO$_4$) and concentrated. The residue was chromatographed on SiO$_2$ (6g) with methylene chloride/2-propanol (97:3) to provide the title compound as a yellow solid after trituration with diisopropyl ether.

Anal. Calcd for C$_{25}$H$_{20}$N$_2$O$_5$S.0.5C$_3$H$_8$O: C, 64.89; H, 4.94; N, 5.72.
Found: C, 65.15; H, 5.00; N, 5.68.

EXAMPLE 9

Diphenylmethyl 7-amino-3-(2-benzyloxy-3,4-dioxo-1-cyclobutenyl)-3-cephem-4-carboxylate (Ib$_4$)

Diphenylmethyl 7-(t-butoxycarbonylamino)-3-(2-benzyloxy-3,4-dioxo-1-cyclobutenyl)-3-cephem-4-carboxylate was deprotected with a solution of pTSOH.H$_2$O in acetonitrile as described in the preceding experiment to provide the title compound which was directly used in the next step.

EXAMPLE 10

(±)-t-Butyl 7-amino-3-(2-amino-3,4-dioxo-1-cyclobutenyl)-1-carba(1-dethia)-3-cephem-4-carboxylate (Ib$_5$)

A solution of (±)-t-butyl 7-(benzyloxycarbonylamino)-3-(2-amino-3,4-dioxo-1-cyclo-butenyl)-1-carba(1-dethia)-3-cephem-4-carboxylate (400 mg) in tetrahydrofuran (100 mL) containing 20% palladium hydroxide (300 mg) was shaken with hydrogen at an initial pressure of 50 psi for 0.66 hr. The mixture was filtered and the filtrate concentrated to dryness. A solution of the residual solid in dimethyl sulfoxide (1 mL) was applied to a Michel-Miller HPLPLC column (22×130 mm) containing Partisil Prep 40 ODS-3. The column was eluted with H$_2$O (100 mL) to remove the dimethyl sulfoxide. The column was then eluted with a step gradient of H$_2$O-acetonitrile (80:20) to H$_2$O-acetonitrile (40:60). The appropriate fractions were combined and the acetonitrile removed on a rotary evaporator. The H$_2$O was removed to provide the title compound (63 mg) and recovered the starting material (195 mg) as yellow solids.

EXAMPLE 11 t-Butyl (6R,7S)-7-amino-3-(2-amino-3,4-dioxo-1-cyclobutenyl)-1-carba(1-dethia)-3-cephem-4-carboxylate (Ib$_5$')

A solution of t-butyl (6R,7S)-7-(benzyloxycarbonylamino)-3-(2-amino-3,4-dioxo-1-cyclobutenyl)-1-carba(1-dethia)-3-cephem-4-carboxylate (365 mg) in N,N-dimethylformamide (8 mL) containing 10% palladium on carbon (200 mg) and 1.0 N HCl (0.70 mL) was shaken with hydrogen at 30 psi for 0.75 hr. The mixture was filtered and the filtrate applied to a Michel-Miller HPLPC column (22×300 mm) containing Partisil Prep 40 ODS-3. The column was eluted with water (200 mL) and then with water-acetonitrile (70:30) to give the product containing fractions. The acetonitrile was removed and the water was removed by lyophilization to leave the title compound (130 mg, 55.6% yield) as a yellow solid.

EXAMPLE 12

Diphenylmethyl 7-[(D)-2-t-butoxycarbonylamino-2-(4-hydroxyphenyl)acetamido]-3-(3,4-dioxo-2-(2-propoxy)-1-cyclobutenyl)-3-cephem-4-carboxylate (Ic$_1$)

(D)-N-t-butoxycarbonyl-2-(4-hydroxyphenyl)glycine (58.3 mg, 0.218 mmol) was added to a stirred solution of diphenylmethyl 7-amino-3-[3,4-dioxo-2-(2-propoxy)-1-cyclobutenyl]-3-cephem-4-carboxylate (100 mg, 0.198 mmol) and EEDQ (54 mg, 0.218 mmol) in ethyl acetate (1 mL). The solution was stirred for 3.5 hr at 22° C. and was diluted with ethyl acetate. The solution was sequentially washed with 1N HCl (2X), dilute NaHCO$_3$ (2X), H$_2$O, and then with saturated NaCl. The solution was partially concentrated and then was diluted with carbon tetrachloride to precipitate the crude product as a yellow solid. Chromatography on SiO$_2$ (10 g) with methylene chloride-methanol (98:2) afforded the title compound (100 mg, 67% yield).

NMR: (CDCl$_3$, 300 MHz) 7.2–7.4 (10H, m), 7.08 (2H, d), 6.9 (1H, s), 6.67 (2H, d), 5.84 (1H, dd), 5.26 (1H, s), 5.2 (1H, m), 4.89 (1H, d), 3.92 (1H, d), 3.32 (1H, d), 1.4 (9H, s), 1.27 (6H, m).

EXAMPLE 13

Diphenylmethyl
7-[2-(2-aminothiazol-4-yl)-(Z)-2-methox-
yiminoacetamido]
-3-(3,4-dioxo-2-methyl-1-cyclobutenyl)-3-cephem-4-
carboxylate (Ic$_2$)

A mixture of diphenylmethyl 7-amino-3-(3,4-dioxo-2-methyl-1-cyclobutenyl)-3-cephem-4-carboxylate (100 mg, 0.217 mmol) and 1-[2-(2-aminothiazo-4-yl)-(Z)-2-methoxyiminoacetyl]-4-methyltetrazole-5-thione (65 mg, 0.217 mmol) in tetrahydrofuran (1 mL) was stirred at 5° C. for 0.25 hr and then for 1 hr at 22° C. when N,N-dimethylformamide (0.05 mL) was added. The solution was diluted with ethyl acetate. The solution was sequentially washed with dilute aqueous NaHCO$_3$ (2X), H$_2$O, and saturated NaCl and then was dried over Na$_2$SO$_4$. Removal of the solvent left a yellow solid which was chromatographed on SiO$_2$ (6 g) with methylene chloride/2-propanol (96:4) to afford the title compound (120 mg, 86% yield) as a yellow powder.

NMR: (CDCl$_3$, 300 MHz) δ (7.64 (1H, d, J=8.9 Hz), 7.3–7.35 (10H, m), 6.89 (1H, s), 6.84 (1H, s), 6.18 (1H, dd, J=8.9 Hz, J=5.2 Hz), 5.4 (2H, broad s), 5.18 (1H, d, J=5.2 Hz), 4.05 (3H, s), 3.91 (1H, d, J=18 Hz), 3.52 (1H, d, J=18 Hz), 1.95 (3H, s).

EXAMPLE 14

Diphenylmethyl
7-[2-(2-aminothiazol-4-yl)-(Z)-2-methox-
yiminoacetamido]-3-3,4-dioxo-2-(2-propoxy)-1-
cyclobutenyl]-3-cephem-4-carboxylate (Ic$_3$)

Acylation of diphenylmethyl 7-amino-3-[3,4-dioxo-2-(2-propoxy)-1-cyclobutenyl]-3-cephem-4-carboxylate (287 mg, 0.569 mmol) with 1-[2-(2-aminothiazol-4-yl)-(Z)-2-methoxyiminoacetyl]-4-methyltetrazole-5-thione (204 mg, 0.683 mmol), according to Example 13, afforded the title compound (373 mg, 93% yield) as a bright yellow solid.

NMR: (CDCl$_3$, 300 MHz) δ 7.78 (1H, d), 7.2–7.4 (10H, m), 6.93 (1H, s), 6.76 (1H, s), 6.14 (1H, dd), 5.4 (2H, broad s), 5.22 (1H, m), 5.13 (1H, d), 4.04 (4H, s, d), 3.47 (1H, d), 1.3 (6H, m).

EXAMPLE 15

Diphenylmethyl
7-[2-(2-aminothiazol-4-yl)-(Z)-2-methox-
yiminoacetamido]-3-(2-amino-3,4-dioxo-1-
cyclobutenyl)-3-cephem-4-carboxylate (Ic$_4$)

Acylation of diphenylmethyl 7-amino-3-(2-amino-3,4-dioxo-1-cyclobutenyl)-3-cephem-4-carboxylate (25 mg, 0.054 mmol) with 1-[2-(2-aminothiazol-4-yl)-(Z)-2-methoxyiminoacetyl]-4-methyltetrazole-5-thione (19.5 mg, 0.066 mmol) in THF (0.25 mL), according to the procedure described in Example 13, afforded the title compound as a granular yellow solid.

NMR: (DMSO-D$_6$, 360 MHz) δ 9.7 (1H, d), 9.03 (1H, s), 8.76 (1H, s), 7.2–7.4 (10H, m), 6.76 (1H, s), 6.72 (1H, s), 5.97 (1H, dd), 5.29 (1H, m), 3.97 (1H, d), 3.85 (3H, s), 3.65 (1H, d).

EXAMPLE 16

Diphenylmethyl
7-[2-(2-aminothiazol-4-yl)-(Z)-2-methox-
yiminoacetamido]-3-(2-benzyloxy-3,4-dioxo-1-
cyclobutenyl)-3-cephem-4-carboxylate (Ic$_5$)

Diphenylmethyl 7-amino-3-(2-benzyloxy-3,4-dioxo-1-cyclobutenyl)-3-cephem-4-carboxylate (544 mg, 0.984 mmol) was acylated with 1-[2-(2-aminothiazol-4-yl)-(Z)-2-methoxyiminoacetyl]-4-methyltetrazole-5-thione (295 mg, 0.984 mmol) in tetrahydrofuran (3 mL), as described in Example 13, to afford the title compound (290 mg, 40% yield) as a yellow solid.

NMR: (CDCl$_3$, 300 MHz) δ 7.72 (1H, d), 7.2–7.4 (15H, m), 6.9 (1H, s), 6.78 (1H, s), 6.12 (1H, dd), 5.5 (3H, m), 5.25 (1H, d), 5.1 (1H, d), 4.12 (1H, d), 4.0 (3H, s), 3.42 (1H, d).

EXAMPLE 17

(±)-t-Butyl
7-[2-(2-aminothiazol-4-yl)-(Z)-2-methox-
yiminoacetamido]-3-(2-amino-3,4-dioxo-1-
cyclobutenyl)-1-carba(1-dethia)-3-cephem-4-carboxy-
late (Ic$_6$)

A solution of (±)-t-butyl 7-amino-3-(2-amino-3,4-dioxo-1-cyclobutenyl)-1-carba(1-dethia)-3-cephem-4-carboxylate (63 mg, 0.189 mmol) and 1-[2-(2-aminothiazol-4-yl)-(Z)-2-methoxyiminoacetyl]-4-methyltetrazole-5-thione (56.6 mg, 0.189 mmol) in tetrahydrofuran (3 mL) was stirred for 1 hr at 22° C. when an additional amount of the tetrazole-5-thione (6 mg) was added. Stirring was continued for 0.25 hr, and the mixture was concentrated. A solution of the residue in ethyl acetate was sequentially washed with dilute aqueous NaHCO$_3$ (2X) and H$_2$O and then was dried (Na$_2$SO$_4$). Removal of the ethyl acetate left the title compound (88 mg, 90% yield) as a yellow granular solid.

EXAMPLE 18

(±)-t-Butyl
7-[2-(aminothiazol-4-yl)-(Z)-2-(2-t-butoxycarbonyl-
prop-2-oxyimino)acetamido]-3-(2-amino-3,4-dioxo-1-
cyclobuten-1-yl)-1-carba(1-dethia)-3-cephem-4-car-
boxylate (Ic$_7$)

2-Mercaptobenzthiazolyl 2-(2-aminothiazol-4-yl)-2-(1-t-butoxycarbonyl-1 -methyl)]ethoxyiminoacetate (72 mg, 0.15 mmol) was added to a stirred solution of (±)-t-butyl 7-amino-3-(2-amino-3,4-dioxo-1-cyclobutenyl)-1-carba(1-dethia)-3-cephem-4-carboxylate (50 mg, 0.15 mmol) in tetrahydrofuran (1 mL). The solution was stirred for 1 hr at 22° C., during which time the title compound crystallized. The bright yellow solid was collected to afford 80 mg of the title compound (83% yield). Recrystallization from tetrahydrofuran provided a sample for characterization.

NMR: (DMSO-D$_6$, 300 mhZ) δ 9.21 (1H,d), 8.92 (1H,s), 8.61 (1H,s), 7.26 (2H,s), 6.71 (1H,s), 5.54 (1H,dd), 3.95 (1H,m), 2.93 (1H,m), 2.22 (1H,m), 1.92 (1H,m), 1.66 (1H,m), 1.40 (24H,m).

EXAMPLE 19 t-Butyl
(6R,7S)-7-[2-(2-aminothiazol-4-yl)-2-(Z)-methoxyiminoacetamido]-3-8
2-amino-3,4-dioxo-1l-cyclobuten-1-yl]-1-carba(1-dethia)-3-cephem-4-carboxylate (Ic$_6$')

In a manner analogous to that described in Example No. 17 for the racemic compound, t-butyl (6R,7S)-7-amino-3-(2-amino-3,4-dioxo-1-cyclobutenyl)-1-carba(1-dethia)-3-cephem-4-carboxylate (130 mg) was acylated with 1-[2-(2-aminothiazol-4-yl)-(Z)-2-methoxyiminoacetyl]-4-methyltetrazole-5-thione (117 mg) to afford the title compound (170 mg, 84% yield) as a yellow granular solid.

EXAMPLE 20

7-[(D)-2-Amino-2-(4-hydroxyphenyl)acetamido1-3-3,4-dioxo-2-(2-propoxy)-1-cyclobutenyl]-3-cephem-4-carboxylic acid (Id$_1$)

Diphenylmethyl 7-[(D)-2-t-butoxycarbonylamino-2-(4-hydroxyphenyl)acetamido]-3-[3,4-dioxo-2-(2-propoxy)-1-cyclobutenyl]-3-cephem-4-carboxylate (154 mg) was added to a stirred, cooled (ice/H$_2$O bath) solution of trifluoroacetic acid (1.8 mL) and anisole (0.2 mL) in methylene chloride (1 mL). Stirring was continued with cooling for 0.25 hr and then for 0.66 hr at ambient temperatures. The solution was concentrated, and the residue was stirred with toluene (20 mL) containing methylene chloride (2 mL) for 0.33 hr to provide the trifluoroacetic acid salt of the title compound (112 mg, 91% yield) as a bright yellow solid.

NMR: (DMSO-D$_6$/D$_2$O, 360 MHz) δ 7.28 (2H, m), 6.80 (2H, m), 5.93 (1H, m), 5.36 (1H, m), 5.2 (1H, s), 3.81 (1H, m), 3.49–3.61 (DOH), 1.39 (6H, m).

Mass Spectrum: (positive ion FAB, NOBA) m/z 488 (M+1).

EXAMPLE 21

7-[2-(2-Aminothiazol-4-yl)-(Z)-2-methoxyiminoacetamido]-3-(3,4-dioxo-2-methyl-1-cyclobutenyl)-3-cephem-4-carboxylic acid (Id$_2$)

Diphenylmethyl 7-[2-(2-aminothiazol-4-yl)-(Z)-2-methoxyiminoacetamido]-3-(3,4-dioxo-2-methyl-1-cyclobutenyl)-3-cephem-4-carboxylate (550 mg) was added to stirred and cooled (ice/H$_2$O bath) trifluoroacetic acid (5 mL) containing anisole (1mL). The cooling bath was removed, and stirring was continued for 0.66 hr at ambient temperatures. The solution was added to stirred diisopropyl ether to precipitate the trifluoroacetic acid salt of the title compound (353 mg, 70% yield) as a yellow powder.

NMR: (DMSO-D$_6$, 300 MHz) δ 9.74 (1H, d), 6.79 (1H, s), 5.98 (1H, dd), 5.32 (1H, d), 3.95 (1H, d), 3.87 (3H, s), 3.71 (1H, d), 2.43 (3H, s).

Mass Spectrum: (Positive ion FAB, NOBA) m/z 478 (M+1).

EXAMPLE 22

7-[2-(2-Aminothiazol-4-yl)-(Z)-2-methoxyiminoacetamido]-3-3,4-dioxo-2-(2-propoxy)-1-cyclobutenyl]-3-cephem-4-carboxylic acid (Id$_3$)

Diphenylmethyl 7-[2-(2-aminothiazol-4-yl)-(Z)-2-methoxyiminoacetamido]-3-[3,4-dioxo-2-(2-propoxy)-1-cyclobutenyl]-3-cephem-4-carboxylate (33 mg) was added to a stirred, cooled (ice/H$_2$O bath) solution of trifluoroacetic acid (100 μL) and anisole (50 μL). The cooling bath was removed, and stirring was continued for 1 hr at ambient temperatures. The solution was diluted with diethyl ether to precipitate the trifluoroacetic acid salt of the title compound as a yellow powder.

NMR: (DMSO-D$_6$, 300 MHz) δ 7.44 (1H, m), 6.76 (1H, s), 5.94 (1H, dd), 5.37 (1H, m), 5.29 (1H, d), 3.92 (1H, d), 3.84 (3H, s), 3.67 (1H, d), 1.41 (6H, m).

EXAMPLE 23

7-[2-(2-Aminothiazol-4-yl)-(Z)-2-methoxyiminoacetamido9
3-(3,4-dioxo-2-hydroxy-1-cyclobutenyl)-3-cephem-4-carboxylic acid (Id$_4$)

A solution of aluminum chloride (82 mg, 0.612 mmol) in nitromethane (1 mL) was added rapidly to a stirred, cooled (ice/H$_2$O bath) solution of diphenylmethyl 7-[2-(2-aminothiazol-4-yl)-(Z)-2-methoxyiminoacetamido]-3-(2-benzyloxy-3,4-dioxo-1-cyclobutenyl)-3-cephem-4-carboxylate (50 mg, 0.068 mmol) and anisole (66 mg, 0.612 mmol) in CH$_2$Cl$_2$ (1 mL). The mixture was stirred with cooling for 0.33 hr and then for 2 hrs at ambient temperatures. The solution was cooled and diluted with dilute aqueous hydrochloric acid to precipitate a solid which was collected and discarded. The aqueous filtrate was washed with ethyl acetate. The aqueous layer was applied to a Michel-Miller HPLPLC column (22×130 mm) containing Partisil Prep 40 ODS-3. The column was eluted with a mixture of H$_2$O-acetonitrile-acetic acid (90:10:0.5). The appropriate fractions were combined and the organic solvents removed. Lyophilization of the aqueous solution afforded the title compound (2.5 mg, 7.7% yield) as a bright yellow solid.

NMR: (DMSO-D$_6$, 300 MHz) δ 9.73 (1H, d), 6.87 (1H, s), 5.78 (1H, dd), 5.18 (1H, d), 4.28 (1H, d), 3.90 (3H, s), 3.55 (1H, d).

Mass Spectrum: (Positive ion FAB, NOBA) m/z 480 (M+1).

EXAMPLE 24

7-[2-(2-Aminothiazol-4-yl)-(Z)-2-methoxyiminoacetamido-]-(2-amino-3,4-dioxo-1-cyclobutenyl)-3-cephem-4-carboxylic acid (Id$_5$)

Diphenylmethyl 7-[2-(2-aminothiazol-4-yl)-(Z)-2-methoxyiminoacetamido]-3-(2-amino-3,4-dioxo-1-cyclobutenyl)-3-cephem-4-carboxylate (400 mg) was added to a stirred, cooled (ice/H$_2$O bath) solution of trifluoroacetic acid (6 mL) and anisole (0.5 mL). The cooling bath was removed and the solution stirred for 0.33 hr at ambient temperatures. The solution was concentrated and the residue macerated with methylene chloride to afford a yellow solid. The solid was dissolved in 0.05M (pH 6.5) ammonium phosphate. The solution was applied to a Michel-Miller HPLPLC column (22×300 mm) containing Partisil Prep 40 ODS-3. The column was eluted with 0.05M (pH 6.5) ammonium phosphate/acetonitrile (90:10). The appropriate fractions were combined and the pH lowered to 3.7 with the addition of dilute hydrochloric acid. The solution was concentrated to a volume of 50 mL when the title compound crystallized (155 mg, 52% yield).

Anal. Calcd for C$_{17}$H$_{14}$N$_6$O$_7$S$_2$.H$_2$O: C, 41.13; H, 3.25; N, 16.93.
Found: C, 41.42; H, 3.10; N, 16.72.

NMR: (DMSO-D6, 300 MHz) δ 9.69 (1H, d), 9.03 (1H, s), 8.75 (1H, s), 7.25 (2H, s), 6.78 (1H, s), 5.90 (1H, dd), 5.27 (1H, d), 3.97 (1H, d), 3.87 (3H, s), 3.64 (1H, d).

EXAMPLE 25

(±)-7-[2-(2-Aminothiazol-4-yl)-(Z)-2-methoxyiminoacetamido]-3-(2-amino-3,4-dioxo-1-cyclobutenyl)-1-carba(1-dethia)-3-cephem-4-carboxylic acid (Id$_6$)

Trifluoroacetic acid (3 L) was added to a stirred, cooled (ice/H$_2$O bath) solution of (±)-t-butyl 7-[2-(2-aminothiazol-4-yl)-(Z)-2-methoxyimino-acetamido]-3-(2-amino-3,4-dioxo-1-cyclobutenyl)-1-carba(1-dethia)-3-cephem-4-carboxylate (88 mg) and anisole (0.2 mL) in methylene chloride (2 mL). The ice bath was removed, and stirring was continued for 0.33 hr at ambient temperatures. The solution was concentrated and was then diluted with diisopropyl ether and reconcentrated. The residual solid was macerated under a mixture of methylene chloride and diisopropyl ether and was collected. The solid was suspended in 0.05M (pH 6.5) ammonium phosphate and several drops of acetonitrile added to effect solution. The solution was chromatographed on a Michel-Miller HPLPLC column (22×130 mm) which contained Partisil Prep 40 ODS-3. The column was eluted with 0.02M (pH 6.5) ammonium phosphate-acetonitrile (90:10). The appropriate fractions were combined and the pH lowered to 3.4 with dilute hydrochloric acid. The solution was concentrated to dryness (5 mm, <30° C.) to leave a yellow solid, which crystallized when triturated with H$_2$O to afford the title compound (30.7 mg, 39% yield).

NMR: (DMSO-D6, 300 MHz) δ 9.32 (1H, d), 8.87 (1H, s), 8.54 (1H, s), 7.19 (2H, s), 6.74 (1H, s), 5.51 (1H, m), 3.83 (1H, m), 3.81 (3H, s), 2.94 (1H, m), 2.21 (1H, m), 1.92 (1H, m), 1.59 (1H, m).

EXAMPLE 26

(±)-7-[2-Aminothiazol-4-yl)-(Z)-2-(2-carboxyprop-2-oxyimino)acetamido]-3-[2-amino-3,4-dioxo-1-cyclobutenyl]-1-carba(1-dethia)-3-cephem-4-carboxylic acid (Id$_7$)

Trifluoroacetic acid (1 mL) was added to a stirred, cooled (ice/H$_2$O bath) solution of (±)-t-butyl 7-[2-aminothiazol-4-yl)-(Z)-2-(2-t-butoxycarbonylprop-2-oxyimino)acetamido]-3-[2-amino-3,4-dioxo-1-cyclobuten-1-yl]-1-carba(1-dethia)-3-cephem-4-carboxylate (50 mg) and anisole (0.1 mL) in methylene chloride (1 mL). The ice bath was removed and stirring was continued for 0.5 hr. at ambient temperatures. The solution was concentrated and then was diluted with diisopropyl ether and reconcentrated. The residual solid was macerated with diisopropyl ether and was collected. The solid was suspended in 0.05 M (pH 6.5) ammonium phosphate and several drops of dilute sodium bicarbonate were added to effect solution. The solution was chromatographed on a Michel-Miller HPLPLC column (22×130 mm) which contained Partisil Prep 40 ODS-3. The column was eluted with 0.05 M (pH 6.5) ammonium phosphate-acetonitrile (90:10). The appropriate fractions were combined and the pH lowered to 3.1 with dilute hydrochloric acid. The acetonitrile was removed and the aqueous solution lyophilized. The residual solid was macerated with a small volume of cold H$_2$O to afford the title compound (27.1 mg, 65.6% yield) as a granular solid.

NMR: (DMSO-D6/D2O, 300 MHz) δ 6.72 (1H,s), 5.41 (1H,d), 3.85 (1H,m), 2.96 (1H,m), 2.32 (1H,m), 1.92 (1H,m), 1.66 (1H,m), 1.41 (3H,s), 1.39 (3H,s). Mass Spectrum: (positive ion FAB, NOBA) m/z 533 (M+1).

EXAMPLE 27

(6R,7S)-7-[2-(2-Aminothiazol-4-yl)-(Z)-2-methoxyiminoacetamido]-3-2-amino-3,4-dioxo-1-cyclobutenyl]-1-carba(1-dethia)-3-cephem-4-carboxylic acid (Id$_6'$)

In a manner analogous to that described in Example 25 for the racemic compound, t-butyl (6R,7S)-7-[2-(2-aminothiazol-4-yl)-(Z)-2-methoxyiminoacetamido]-3-(2-amino-3,4-dioxo-1-cyclobuten-1-yl]-1-carba(1-dethia)-3-cephem-4-carboxylate (170 mg) was deprotected with TFA in the presence of anisole to afford the title compound (38.5 mg, 25% yield).

NMR: (DMSO-D6/D2O, 300 MHz) δ 6.74 (1H,s), 5.41 (1H,s), 3.84 (1H,m), 3.82 (3H,s), 2.96 (1H,m), 2.32 (1H,m), 1.89 (1H,m), 1.59 (1H,m).

EXAMPLE 28

Preparation of (±)-t-Butyl 7-(benzyloxycarbonylamino)-3-trifluoromethylsulfonyloxy-1-carba(1-dethia)-3-cephem-4-carboxylate (IIIa)

a. (±)-t-Butyl 2-[cis-3-phthalyimido-4-(2-(2-furyl)ethenyl)-2-oxoazetidin-1-yl]acetate 3-(2-Furyl)acrolein (1.22 g, 0.010 mmol) was added to a stirred, cooled (ice/H$_2$O bath) solution of t-butyl glycinate (1.31 g, 0.010 mol) in methylene chloride (30 mL). The ice bath was removed, and stirring was continued for 18 hr when 4 A° activated molecular sieves (4 g) were added. After 2 hr, the mixture was filtered and the sieves washed with additional methylene chloride. The filtrate was concentrated to a volume of 35 mL. Triethylamine (1.53 mL, 0.01 mol) was added, and the solution of the crude imine was cooled with a dry ice-/acetone bath maintained at −20° C. A solution of 1,3-dioxo-2-isoindolineacetyl chloride (1.79 g, 8.5 mmols) in methylene chloride (8 mL) was added dropwise during 5 minutes. Stirring was continued for 0.33 hr at a bath temperature of −20° C. The mixture was allowed to warm to 22° C. and then was sequentially washed with H$_2$O (2X), dilute hydrochloric acid, H$_2$O, dilute NaHCO$_3$, H$_2$O, and saturated NaCl. The solution was dried over MgSO$_4$ and concentrated. The residual froth was crystallized from methanol to provide the title compound (1.7 g, 47% yield) as pale yellow Anal. Calcd for $C_{23}H_{22}N_2O_6$: C, 65.40; H, 5.25; N, 6 64.

Found: C, 64.98; H, 5.06; N, 6.57.

b. (±)-t-Butyl 2-[cis-3-phthalylimido-4-(2-(2-furyl)ethyl)-2-oxoazetidin-1-yl]acetate A mixture of (±)-t-butyl 2-[cis-3-phthalylimido-4-(2-(2-furyl)ethenyl)-2-oxoazetidin-1-yl]acetate (1.0 g), 5% palladium on carbon (500 mg) and 95% ethanol (100 mL) was shaken with hydrogen at an initial pressure of 50 psi for 0.75 hr. The mixture was filtered and the filtrate concentrated to dryness to afford the title compound as a colorless crystalline solid. Recrystallization from 95% ethanol provided an analytical sample, mp 150°–151° C.

Anal. Calcd for $C_{23}H_{24}N_2O_6$: C, 65.09; H, 5.70; N, 6.60.

Found: C, 65.08; H, 5.68; N, 6.54.

c. (±)-t-Butyl 2-[cis-3-amino-4-(2-(2-furyl)ethyl)-2-oxoazetidin-1-yl]acetate

A solution of methylhydrazine (0.585 mL, 0.011 mol) and (±)-t-butyl 2-[cis-3-phthalylimido-4-(2-(2-furyl)ethyl)-2-oxoazetidin-1-yl]acetate (4.24 g, 0.010 mol) in absolute ethanol (50 mL) was stirred under reflux and under a nitrogen atmosphere for 2 hrs. The mixture was cooled to 22° C. and the solids removed by filtration. The filtrate was concentrated to dryness, and the residual solids were extracted with methylene chloride (3×). The combined extracts were filtered and the filtrate concentrated to dryness. The residue was extracted with boiling cyclohexane (2×100 mL). The combined extracts were filtered and were concentrated by boiling to a volume of 80 mL. Upon cooling, the title compound (2.77 g, 94% yield) crystallized. An analytical sample was previously obtained from an analogous small scale experiment, mp 85°–87° C. (cyclohexane).

Anal. Calcd for $C_{15}H_{22}N_2O_4$: C, 61.21; H, 7.54; N, 9.52.

Found: C, 60.60; H, 7.55; N, 9.82.

d. (±)-t-Butyl 2-[cis-3-benzyloxycarbonylamino-4-(2-(2-furyl)ethyl)-2-oxoazetidin-1-yl]acetate A solution of benzyl chloroformate (485 μL, 3.4 mmols) in methylene chloride (2.5 mL) was added dropwise to a stirred, cooled (ice/H$_2$O bath) solution of (±)-t-butyl 2-[cis-3-amino-4-(2-(2-furyl)ethyl)-2-oxoazetidin-1-yl]acetate (1.0 g, 3.4 mmols) and diisopropylethylamine (592 μL, 3.4 mmols) in methylene chloride (10 mL). Stirring was continued with cooling for 0.5 hr and then for 0.33 hr at ambient temperatures. The solution was sequentially washed with 0.5M (ph 4) ammonium phosphate, H$_2$O, dilute aqueous NaHCO$_3$, and saturated NaCl. The solution was dried (Na$_2$SO$_4$) and concentrated, and the residue was chromatographed on SiO$_2$ (50 g) with hexane-ethyl acetate (2:1). The appropriate fractions were combined and concentrated to leave a viscous oil which was crystallized from diethyl ether-hexane to afford the title compound (1.05 g, 72% yield).

NMR: (CDCl$_3$, 300 MHz) δ 7.32 (5H, s), 7.26 (1H, m), 6.25 (1H, m), 5.94 (1H, m), 5.49 (1H, d), 5.14 (1H, m), 5.10 (2H, s), 4.03 (1H, d), 3.93 (1H, m), 3.58 (1H, d), 2.61 (2H, t), 1.74–1.98 (2H, m), 1.43 (9H, s).

e. (±)-t-Butyl 2[-cis-3-benzyloxycarbonylamino-4-(2-carboxyethyl)-2-oxoazetidin-1-yl]acetate A solution of (±)-t-butyl 2-[cis-3-benzyloxycarbonylamino-4-(2-(2-furyl)ethyl)-2-oxoazetidin-1-yl]acetate (100 mg) and sudan red 7B (0.2 mg) in 6 mL of methanol-methylene chloride (1:1) was cooled to −78° C. Ozone/oxygen was bubbled in to the solution up to the endpoint of sudan red. The solution was allowed to warm to ambient temperature when 0.25N NaOH (1.87 mL) and 30% hydrogen peroxide (0.25 mL) were added. The solution was stirred for 2 hrs and was then diluted with H$_2$O. The organic solvents were removed, and the aqueous solution was washed with ethyl acetate. The aqueous solution was layered with ethyl acetate and the pH of the mixture lowered to 3.7 with dilute hydrochloric acid. The ethyl acetate layer was washed (saturated NaCl), dried (NaSO$_4$), and concentrated. The residue was crystallized from diethyl ether to provide the title compound (44 mg, 46% yield), mp 118°–120° C. Recrystallization from ethyl acetate-hexane provided colorless crystals of the analytical sample.

Anal. Calcd for $C_{20}H_{26}N_2O_7$: C, 59.11; H, 6.45; N, 6.88.

Found: C, 58.88; H, 6.47; N, 6.60.

f. (±)-t-Butyl 2-[cis-3-benzyloxycarbonylamino-4-(2-(2-pyridylthiocarbonyl)ethyl)-2-oxoazetidin-1-yl]acetate Dicyclohexylcarbodiimide (223 mg, 1.08 mmols) was added to a stirred, cooled (ice/H$_2$O bath) solution of (±)-t-butyl 2-[cis-3-benzyloxycarbonylamino-4-(2-carboxyethyl)-2-oxoazetidin-1-yl]acetate (440 mg, 1.08 mmols) in methylene chloride (5 mL). The mixture was stirred for 3 minutes when the cooling bath was removed and when 2-mercaptopyridine (120 mg, 1.08 mmols) was added. The mixture was stirred for 1.25 hr and was then diluted with methylene chloride and filtered. The filtrate was sequentially washed with dilute aqueous NaHCO$_3$, H$_2$O, and saturated NaCl. The solution was concentrated and the residue crystallized from ethyl acetate-hexanes to afford the title compound (290 mg, 54% yield).

Anal. Calcd for $C_{25}H_{29}N_3O_6S$: C, 60.11; H, 5.86; N, 8.42.

Found: C, 59.66; H, 5.93; N, 8.35.

g. (±)-t-Butyl 7-(benzyloxycarbonylamino)-3-trifluoromethylsulfonyloxy-1-carba(1-dethia)-3-cephem-4-carboxylate (IIIa)

A 1.0M solution in tetrahydrofuran of sodium bis(trimethylsilyl)amide (47 mL, 0.047 mol), which was precooled to −78° C., was rapidly added to a stirred solution at −78° C. of (±)-t-butyl 2-[cis-3-benzyloxycarbonylamino-4-(2-(2-pyridylthiocarbonyl)ethyl)-2-oxoazetidin-1-yl]acetate (7.8 g, 0.0156 mol) in tetrahydrofuran (115 mL). The cooling bath was removed and the solution allowed to stir until the internal temperature rose to −30° C. The solution was poured into saturated ammonium chloride (250 mL) containing 85% H$_3$PO$_4$ (4 mL). The pH of the stirred mixture was adjusted to about 4.3 with the addition of 85% H$_3$PO$_4$. The mixture was extracted with ethyl acetate (3×200 mL). The combined extracts were washed with H$_2$O (3×), dried (Na$_2$SO$_4$), and concentrated. The residue was chromatographed on SiO$_2$ (100 g), impregnated with silver nitrate (5%), via the flash technique, with ethyl acetate-hexanes (60:40) to afford (±)-t-butyl 7-(benzyloxycarbonylamino)-3-hydroxy-1-carba(1-dethia)-3-cephem-4-carboxylate, which was isolated as a colorless froth (3.44 g, 57% yield) and which was used directly in the next step.

Trifluoromethanesulfonic anhydride (1.49 mL, 8.86 mmols) was added to a stirred solution at −78° C. of the enolic 1-carbacephem (3.44 g, 8.86 mmols) and diisopropylethylamine (1.54 mL, 8.86 mmols) in methylene chloride (100 mL). The mixture was stirred for 0.33 hr and then was allowed to warm to 0° C. The solution was washed with H$_2$O (3×), dried (Na$_2$SO$_4$), and concentrated to a volume of about 50 mL. Dilution with diisopropyl ether and additional concentration resulted in crystallization of the title compound (2.94 g). Analytical HPLC indicated a purity of >99 area percent.

HPLC: (retention time=10.88 minutes). Waters $C_{18}$ radial pak cartridge. 2.0 mL/min. of 25% pump A (H$_2$O) and 75% of pump B (80% acetonitrile—20% H$_2$O). Detect at 254 nm.

EXAMPLE 29

(±)-t-Butyl 7-phenoxyacetamido-3-trifluoromethylsulfonyloxy-1-carba(1-dethia)-3-cephem-4-carboxylate (IIIb)

Trifluoromethanesulfonic anhydride (65 μL, 0.386 mmol) was added to a stirred solution at −78° C. of (±)-t-butyl 7-phenoxyacetamido-3-hydroxy-1-carba(1-dethia)-3-cephem-4-carboxylate (150 mg, 0.386 mmol) and diisopropylethylamine (67 μL, 0.386 mmol) in methylene chloride (3 mL). The mixture was stirred for 0.2 hr and was diluted with methylene chloride. The solution was washed with $H_2O$ (2×), dried ($MgSO_4$), and concentrated. Trituration of the residue with diethyl ether afforded colorless crystals of the title compound (136 mg, 68% yield).

NMR: ($CDCl_3$, 300 MHz) δ 6.82–7.35 (6H, m), 5.36 (1H, m), 4.5 (2H, s), 3.94 (1H, m), 2.54 (2H, m), 2.1 (1H, m), 1.58 (1H, m), 1.49 (9H, s).

EXAMPLE 30

Synthesis of t-Butyl (6R,7S)-7-(benzyloxycarbonylamino)-3-trifluoromethylsulfonyloxy-1-carba(1-dethia)-3-cephem-4-carboxylate (IIIa')

a. (3S,4R)-3-Benzyloxycarbonylamino-4[-2-(2-furyl)ethyl]azetidin-2-one

A solution of benzyl chloroformate (5.4 mL, 0.0378 mol) in methylene chloride (10 mL) was added dropwise during 0.25 hr to a stirred, cooled (ice/$H_2O$ bath) of (3S,4R)-3-amino-4-[2-(2-furyl)ethyl]azetidin-2-one (6.82 g, 0.0378 mol) and diisopropylethylamine (6.6 mL, 0.0378 mol) in methylene chloride (75 mL). Stirring was continued with cooling for 2 hr and then for 0.5 hr at ambient temperatures. The mixture was diluted with additional methylene chloride and was sequentially washed with $H_2O$, dilute hydrochloric acid, $H_2O$, dilute aqueous $NaHCO_3$, $H_2O$ and saturated NaCl. The solution was dried over $MgSO_4$ and concentrated. The residue was crystallized from ethyl acetate to afford the title compound (7.05 g, 60% yield) as an off-white solid.

b. t-Butyl (3S,4R)-2-[3-benzyloxycarbonylamino-4-(2-(2-furyl)ethyl)-2-oxoazetidin-1-yl]acetate Triton B (1.94 mL, 4.3 mmols) was added dropwise to a stirred, cooled (−30° C.) solution of (3S,4R)-3-benzyloxycarbonylamino-4-[2-(2-furyl)ethyl]azetidin-2-one (1.35 g, 4.3 mmols) in N,N-dimethylformamide (15 mL). Stirring was continued for 0.25 hr. at −30° C. The mixture was allowed to warm to 0° C. during about 0.25 hr and then was recooled to −30° C. when a solution of t-butyl bromoacetate (0.764 mL, 4.73 mmols) in DMF (3 mL) was added dropwise. Stirring was continued at −30° C. for 0.25 hr., 1hr at 0° C. and then for 2 hr at ambient temperatures, when additional t-butyl bromoacetate (0.3 mL) was added. The mixture was stirred for an additional 1hr and was poured into $H_2O$. The mixture was extracted twice with ethyl acetate. The extracts were washed twice with $H_2O$, followed by saturated NaCl and then dried over $MgSO_4$. The ethyl acetate was removed and the residue flash chromatographed on $SiO_2$ (40 g) with methylene chloride-methanol (98:2) to afford 1.47 g (80% yield) of the title compound as a viscous oil which crystallized. Recrystallization from ethyl acetate-hexanes afforded colorless crystals, mp 82–84° C.

NMR: ($CDCl_3$, 300 MHz) δ 7.31 (5H,s), 7.26 (1H,m), 6.23 (1H,m), 5.94 (1H,m), 5.57 (1H,d), 5.12 (1H,m), 5.09 (2H,s), 4.02 (1H,m), 3.92 (1H,m), 3.57 (1H,m) 2.59 (2H,m), 1.92 (1H,m), 1.82 (1H,m), 1.42 (9H,s).

c. t-Butyl (3S,4R)-2-[3-benzyloxycarbonylamino-4-(2-carboxyethyl)-2-oxoazetidin-1-yl]acetate In a manner analogous to that described in Example 28(e) for the racemic compound, t-butyl (3S,4R)-2-[3-benzyloxycarbonylamino-4-(2-(2-furyl)ethyl)-2-oxoazetidin-1-yl]acetate (5.0 g) was ozonized to provide the title compound (4.8 g) which was rapidly chromatographed on $SiO_2$ (20 g) with methylene chloride-methanol (95:5) to provide the purified title compound as a colorless froth (3.5 g, 73.8% yield).

d. t-Butyl (3S,4R)-2[-3-benzyloxycarbonylamino-4-(2-(2-pyridylthiocarbonyl)ethyl)-2-oxoazetidin-1-yl]acetate In a manner analogous to that described in Example 28(f) for the racemic compound, t-butyl (3S,4R)-2-[3-benzyloxycarbonylamino-4-(2-carboxyethyl)-2-oxoazetidin-1-yl]acetate (3.5 g) was converted to the title compound (4.5 g), which was isolated as a viscous gum.

d. t-Butyl (6R,7S)-7-(benzyloxycarbonylamino)-3-trifluoromethylsulfonyloxy-1-carba(1-dethia)-3-cephem-4-carboxylate (IIIa')

In a manner analogous to that described in Example 28(g) for the racemic compound, t-butyl (3S,4R)-2-[3-benzyloxycarbonylamino-4-(2-(2-pyridylthiocarbonyl)ethyl)-2-oxoazetidin-1-yl]acetate (4 g) was subjected to the Dieckman cyclization to afford t-butyl (6R,7S)-7-(benzyloxycarbonylamino)-3-hydroxy-1-carba(1-dethia)-3-cephem-4-carboxylate (1.5 g) which was isolated as a tacky froth and which was directly contacted with trifluoromethanesulfonic anhydride in the presence of diisopropylethylamine to afford the title compound (1.6 g) as a viscous gum.

EXAMPLE 31

4-(2-Propoxy)-3-(tri-n-butylstannyl)cyclobut-3-ene-1,2-dione ($V_1$)

A solution of 0.052M n-$Bu_4N^+CN^-$ in tetrahydrofuran (7.69 mL, 0.4 mmol) was added dropwise to a stirred solution at −20° C. of diisopropyl squarate (3.96 g, 0.020 mol) and n-$Bu_3SnSi(CH_3)_3$ (7.27 g, 0.020 mol) in tetrahydrofuran (154 mL). Stirring was continued at −20° C. for 2 hrs. The solution was concentrated and the residue chromatographed on $SiO_2$ with diethyl ether-hexane (10:90) to afford the title compound (5.75 g, 67% yield) as a yellow oil.

NMR: ($CDCl_3$, 300 MHz) δ 5.31 (1H, m), 1.4–1.5 (6H, m), 1.35 (6H, d), 1.13–1.29 (6H, m), 1.02–1.1 (6H, m), 0.75–0.84 (9H, m).

EXAMPLE 32

4-Benzyloxy-3-(tri-n-butylstannyl)cyclobut-3-ene-1,2-dione ($V_2$)

In a similar manner, replacement of the diisopropyl squarate in Example 31 with dibenzyloxy squarate afforded the title compound (71% yield) as a yellow oil.

NMR: ($CDCl_3$ 300 MHz) δ 7.4 (5H, s), 5.72 (2H, s), 1.44–1.58 (6H, m), 1.2–1.34 (6H, m), 1.1–1.2 (6H, m), 0.8–0.9 (9H, m).

EXAMPLE 33

4-Allyloxy-3-(tri-n-butylstannyl)cyclobut-3-ene-1,2-dione (V$_3$)

In a similar manner to that described in Example 31, replacement of the diisopropyl squarate with diallyloxy squarate afforded the title compound (18% yield) as a yellow oil.

NMR: (CDCl$_3$, 300 MHz) δ 5.89–6.06 (1H, m), 5.3–5.47 (2H, m), 5.08–5.17 (2H, m), 1.43–1.59 (6H, m), 1.2–1.34 (6H, m), 1.08–1.17 (6H, m), 0.079–0.089 (9H, m).

EXAMPLE 34

2,2-Ethylenedioxy-4-methyl-3-(tri-n-butylstannyl)cyclobut-3-ene-1-one (XIII$_1$)

Triethylamine (28 mL, 0.20 mol) and chlorotrimethylsilane (13 mL, 0.10 mol) were successively added to a stirred solution of 3,4-diisopropoxy-2-hydroxy-2-methylcyclobut-3-ene-1-one (14.3 g, 0.0667 mol) in diethyl ether (250 mL). The mixture was allowed to stir at ambient temperatures for 18 hrs. The mixture was filtered through SiO$_2$ contained in a sintered glass funnel. The filter cake was washed with additional diethyl ether. The ether was removed to leave 3,4-diisopropoxy-2-trimethylsilyloxy-2-methylcyclobut-3-ene-1-one (18 g, 94% yield) as a clear oil. Trimethylsilyl trifluoromethanesulfonate (150 μL, 0.78 mmol) was added to a stirred solution of the silyl ether (18 g, 0.0628 mol) and 1,2-bis(trimethylsilyloxy)ethane (16.2 mL, 0.066 mmol) in tetrahydrofuran (36 mL). The solution was stirred for 1 hr at 22° C. and additional trimethylsilyl trifluoromethanesulfonate (150 μL) was then added. The solution was stirred for an additional 0.25 hr and was concentrated to dryness. The residue was flash chromatographed on SiO$_2$(200 g) with diethyl ether-hexanes (1:1) to afford 2,2-ethylenedioxy-3-isopropoxy-4-methylcyclobut-3-ene-1-one (9 g, 73% yield) as a colorless crystalline solid. A solution of n-Bu$_4$N+CN$^-$ (140 mg, 0.52 mmol) in tetrahydrofuran (4 mL) was added dropwise to a stirred solution of the ketal (2.0 g, 0.010 mol) and n-Bu$_3$SnSi(CH$_3$)$_3$ (4.03 g, 0.011 mol) in tetrahydrofuran (60 mL) at 22° C. Stirring was continued for 0.66 hr, and the dark solution was concentrated to dryness. The residue was flash chromatographed on SiO$_2$ (80 g) with hexane and then with diethyl ether-hexane (25:75) to afford the title compound as a yellow oil (4.11 g, 95% yield).

NMR: (CDCl$_3$, 300 MHz) δ 3.9–4.1 (4H, m), 1.82 (3H, s), 1.38–1.54 (6H, m), 1.14–1.31 (6H, m), 0.96–1.06 (6H, m), 0.76–0.85 (9H, m).

EXAMPLE 35

4-Methyl-3-(tri-n-butylstannyl)cyclobut-3-ene-1,2-dione (V$_4$)

2,2-Ethylenedioxy-4-methyl-3-(tri-n-butylstannyl)cyclobut-3-ene-1-one (450 mg) was added to a stirred mixture of tetrahydrofuran (4 mL) and sulfuric acid-H$_2$O (3 mL of 1:1). The mixture was stirred at 22° C. for 2.5 hrs and then was diluted with H$_2$O. The mixture was extracted with n-heptane (2×). The combined extracts were sequentially washed with H$_2$O (2×) and saturated NaCl, dried (Na$_2$SO$_4$), and concentrated to leave the title compound (145 mg, 36% yield) as a yellow oil.

NMR: (CDCl$_3$, 300 MHz) δ 2.42 (3H, s), 1.44–1.56 (6H, m), 1.21–1.35 (6H, m), 1.12–1.20 (6H, m), 0.081–0.90 (9H, m).

EXAMPLE 36

4-Amino-3-(tri-n-butylstannyl)cyclobut-3-ene-1,2-dione (V$_6$)

Ammonia was bubbled into a stirred, cooled (ice/H$_2$O bath) solution of 4-allyloxy-3-(tri-n-butylstannyl)cyclobut-3-ene-1,2-dione (450 mg) in hexane-diethyl ether (8 mL of 1:1) for about 0.25 hr. The mixture was concentrated and the residue chromatographed on SiO$_2$ (19 g) with diethyl ether-hexane (1:1) to afford the title compound (350 mg, 86% yield) as a tan crystalline solid.

Anal. Calcd for C$_{16}$H$_{29}$NO$_2$Sn: C, 49.78; H, 7.58; N, 3.63.
Found: C, 50.17; H, 7.86; N, 3.70.

NMR: (CDCl$_3$, 300 MHz) δ 7.24 (1H, broad s), 6.89 (1H, broad s), 1.43–1.6 (6H, m), 1.35–1.22 (6H, m), 1.12–1.20 (6H, m), 0.077–0.087 (9H, m).

EXAMPLE 37

4-(4-Methylpiperazinyl)-3-(tri-n-butylstannyl)-cyclobut-3-ene-1,2-dione (V$_7$)

1-Methylpiperazine (0.65 g, 6.49 mmols) was added to a stirred, cooled (ice/H$_2$O bath) solution of 4-(2-propoxy)-3-(tri-n-butylstannyl)-cyclobut-3-ene-1,2-dione (2.53 g, 5.90 mmols) in diethyl ether (80 mL). Stirring was continued with cooling for 1 hr and then at ambient temperatures for 1 hr. The mixture was concentrated and the residue chromatographed on SiO$_2$ with ethyl acetate-methylene chloride (35:65) to afford the title compound (2.1 g, 76% yield) as a golden viscous oil.

Anal. Calcd for C$_{21}$H$_{38}$N$_2$O$_2$SN: C, 53.75; H, 8.16; N, 5.97.
Found: C, 53.92; H, 8.03; N, 5.97.

EXAMPLE 38

4-Ethylamino-3-(tri-n-butylstannyl)cyclobut-3-ene-1,2-dione (V$_8$)

Using the procedure described in Example 37 treatment of 4-(2-propoxy)-3-(tri-n-butylstannyl)cyclobut-3-ene-1,2-dione with anhydrous monoethyl amine afforded the title compound as a dark viscous oil which crystallized.

Anal. Calcd for C$_{18}$H$_{33}$NO$_2$SN: C, 52.21; H, 8.04; N, 3.39.
Found: C, 51.67; H, 7.74; N, 3.21.

Mass Spectrum: (direct chemical conization, isobutane) m/z 416 (M+1).

EXAMPLE 39

1[2-(2-(2-aminothiazol-4-yl-(Z)-2-methoxyiminoacetyl]-4-methyltetrazole-5-thione An oven-dried 1,000 mL 3-necked flask equipped with an overhead stirrer was cooled to room temperature under a stream of dry nitrogen. The flask was charged with 500 mL dry acetone (4 A sieves) 20.8 g (0.1 mol, 1.0 equiv) of 1,3-dicyclohexylcarbodiimide (DCC, Aldrich, 99%, 11.6 g (0.1 mol, 1.0 equiv) of 2-mercapto-1-methyltetrazole, 20.12 g (0.1 mol, 1.0 equiv) of 2-(2-aminothiazol-4-yl)-(Z)-2-methoxyiminoacetic acid and 500 mL of dry acetone. The resulting slurry was stirred at ambient temperature. The progress of the reaction was monitored by HPLC. After ca. 24 hr, the slurry was cooled to 0°–5° C. and was stirred for 45 min. The solid was collected by filtration and was washed with dry acetone (2×60 mL). The product was precipitated by dropwise addition of 4,000 mL of hexanes to the acetone solution at 0°–5° C. The solid was filtered, washed with cold (0°–5° C.) 4/1 (v/v) hexanes/acetone (2×50 mL) and was partially dried under suction for 15 min. The powder was further dried at 43° C. in vacuo for 16 hrs to afford 10.54 g (35%) of the title product as a light yellow powder. This material was used as is without further purification.

EXAMPLE 40

Biological Tests

The in vivo therapeutic efficacy of two representative compounds after intramuscular administration to mice infected intraperitoneally with 0.5 ml of various bacterial suspension is shown in Table I. The values are given in $PD_{50}$ (dose in mg/kg) to give protection to 50% of the infected mice.

Also included in the table is the in vitro MIC's.

TABLE I

| Compound | MIC (mcg/ml) vs. E. coli A15119 | $PD_{50}$ (mg/kg) i.m. vs E. coli A15119 41 $LD_{50}$ | 143 $LD_{50}$ |
|---|---|---|---|
| $Id_3$ | 1 | 1.4 | >25 |
| $Id_6$ | 0.06 | <0.098 | 1.7 |

What is claimed is:

1. A compound of formula I

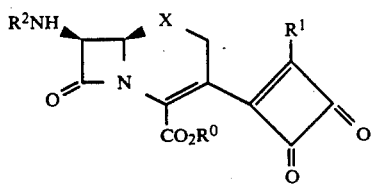

wherein
X is sulfur;
$R^1$ is hydrogen, hydroxy, amino, $C_{1-6}$ alkyl, $C_{2-6}$ alkenyl, $C_{2-6}$ alkynyl, phenyl optionally substituted with one to three $C_{1-6}$ alkyl, $C_{1-6}$ alkyloxy or hydroxy, $C_{1-6}$ alkylthio, phenylthio optionally substituted with one to three $C_{1-6}$ alkyl or $C_{1-6}$ alkyloxy on the phenyl ring, phenylmethyloxy optionally substituted with one to three $C_{1-6}$ alkyl or $C_{1-6}$ alkyloxy on the phenyl ring, 1-morpholino, $C_{1-6}$ alkyloxy, $C_{2-6}$ alkenylmethyloxy, $C_{3-6}$ alkynylmethyloxy, $C_{1-6}$ alkylamino, $C_{1-6}$ dialkylamino or a radical selected from the group consisting of

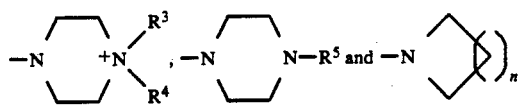

in which n is 0 to 3, $R^5$ is $C_{1-6}$ alkyl or hydrogen, and $R^3$ and $R^4$ are independently $C_{1-6}$ alkyl;
$R^2$ is an acyl group;
$R^0$ is hydrogen or a conventional carboxy protecting group, or $-CO_2R^0$ taken together forms a physiologically hydrolyzable ester; or
pharmaceutically acceptable salts or solvates thereof.

2. A compound of claim 1 in which $R^0$ is hydrogen or $-CO_2R^0$ taken together forms a physiologically hydrolyzable ester.

3. A compound of claim 2 in which $R^2$ is an acyl group represented by the radical $R^aCO-$, wherein $R^a$ is hydrogen;
$C_{1-6}$ alkyl, $C_{1-6}$ alkyl substituted by cyano, carboxy, halogen, amino, $C_{1-4}$ alkoxy, $C_{1-4}$ alkylthio, or trifluoromethylthio;
a phenyl or substituted phenyl group represented by the formula

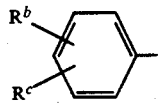

wherein $R^b$ an $R^c$ independently are hydrogen, halogen, hydroxy, $C_{1-4}$ alkoxy, $C_{1-4}$ alkyl, $C_{1-4}$ alkylthio, amino, mono- or di($C_{1-4}$ alkyl)amino, $C_{1-4}$ alkanoylamino, $C_{1-4}$ *alkylsulfonylamino, carboxy, carbamoyl, hydroxymethyl,* aminomethyl, or carboxymethyl;
a group presented by the formula

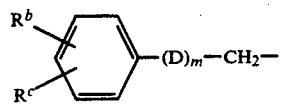

wherein $R^b$ and $R^c$ have the same meanings as defined above, D is oxygen or sulfur, and m is 0 or 1;
a heteroarylmethyl group represented by the formula $R^d-CH_2-$ wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-4}$ alkyl, $C_{1-4}$ alkoxy, $C_{1-4}$ alkysulfonylamino;
a substituted methyl group represented by the formula

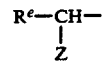

wherein $R^e$ is cyclohex-1,4-dienyl, or a phenyl group or substituted phenyl group

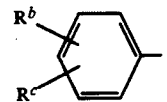

wherein $R^b$ and $R^c$ have the above defined meanings, or $R^e$ is $R^d$ as defined above, and Z is hydroxy, $C_{1-4}$ alkanoyloxy, carboxy, sulfo, or amino;
a keto group or an oximino-substituted group represented by the formulae

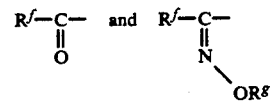

wherein $R^f$ is $R^d$ or $R^e$ as defined above and $R^g$ is hydrogen, $C_{1-6}$ alkyl, cyclic $C_{3-6}$ alkyl or a radical selected from the formulae

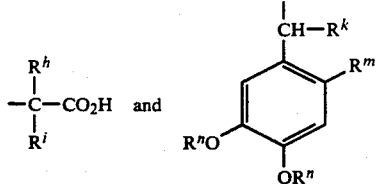

in which $R^h$ and $R^i$ are independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen or carboxy, with the proviso that both cannot be the same, and $R^n$ is hydrogen or acetyl; or an alkylidene group of the formulae

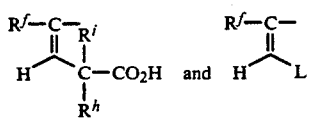

in which L is halogen or $CF_3$, and $R^f$, $R^i$ and $R^h$ are as defined above.

4. A compound of claim 3 wherein $R^a$ is a radical of the formulae

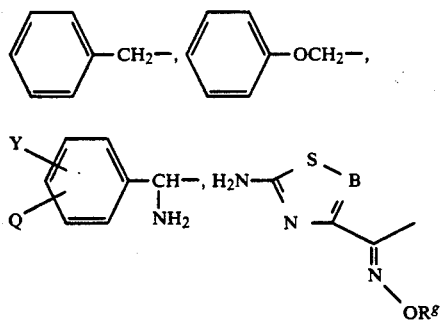

and

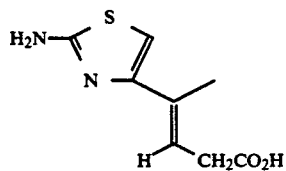

wherein B is nitrogen or CH; Y and Q are independently hydrogen, hydroxy or halogen; and $R^g$ has the above defined meaning.

5. A compound of claim 4 wherein $R^a$ is a radical of the formulae

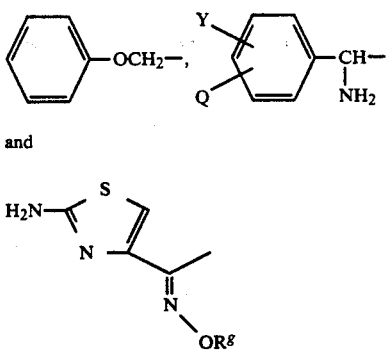

and

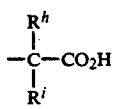

in which $R^g$ is hydrogen, $C_{1-6}$ alkyl, cyclic $C_{3-6}$ alkyl or a radical of the formula $$-\underset{R^i}{\overset{R^h}{C}}-CO_2H$$

in which $R^h$ and $R^i$ are as defined above.

6. A compound of claim 5 in which $R^1$ is hydroxy, amino, $C_{1-6}$ alkyl, $C_{1-6}$ alkyloxy, phenylmethyloxy optionally substituted with one to three $C_{1-6}$ alkyl or $C_{1-6}$ alkyloxy on the phenyl ring, or $C_{2-6}$ alkenylmethyloxy.

7. The compound of claim 6 which is 7-[(D)-2-amino-2-(4-hydroxyphenyl)acetamido]-3-[3,4-dioxo-2-(2-propoxy)-1-cyclobutenyl]-3-cephem-4-carboxylic acid.

8. The compound of claim 6 which is 7-[2-(2-amino-thiazol-4-yl)-(Z)-2-methoxyiminoacetamido]-3-(3,4-dioxo-2-methyl-1-cyclobutenyl)-3-cephem-4-carboxylic acid.

9. The compound of claim 6 which is 7-[2-(2-amino-thiazol-4-yl)-(Z)-2-methoxyiminoacetamido]-3-[3,4-dioxo-2-(2-propoxy)-1-cyclobutenyl]-3-cephem-4-carboxylic acid.

10. The compound of claim 6 which is 7-[2-(2-amino-thiazol-4-yl)-(Z)-2-methoxyiminoacetamido]-3-(3,4-dioxo-2-hydroxy-1-cyclobutenyl)-3-cephem-4-carboxylic acid.

11. The compound of claim 6 which is 7-[2-(2-amino-thiazol-4-yl)-(Z)-2-methoxyiminoacetamido]-3-(2-amino-3,4-dioxo-1-cyclobutenyl)-3-cephem-4-carboxylic acid.

12. A pharmaceutical composition comprising an antibacterial effective amount of a compound as claimed in any one of claims 2 to 11 and a pharmaceutically acceptable carrier or diluent.

13. A method for treating bacterial infection in a mammal, which comprises administering to said mammal an antibacterial effective amount of a compound as claimed in any one of claims 2 to 11.

* * * * *